United States Patent
Preusche

(10) Patent No.: US 10,141,081 B2
(45) Date of Patent: Nov. 27, 2018

(54) PHASE CONTRAST X-RAY IMAGING DEVICE AND PHASE GRATING THEREFOR

(71) Applicant: SIEMENS HEALTHCARE GMBH, Erlangen (DE)

(72) Inventor: Oliver Preusche, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 260 days.

(21) Appl. No.: 15/027,787

(22) PCT Filed: Sep. 26, 2014

(86) PCT No.: PCT/EP2014/070670
§ 371 (c)(1),
(2) Date: Apr. 7, 2016

(87) PCT Pub. No.: WO2015/052017
PCT Pub. Date: Apr. 16, 2015

(65) Prior Publication Data
US 2016/0254069 A1 Sep. 1, 2016

(30) Foreign Application Priority Data

Oct. 7, 2013 (DE) ........................ 10 2013 016 700

(51) Int. Cl.
*G21K 1/00* (2006.01)
*G21K 1/06* (2006.01)
(Continued)

(52) U.S. Cl.
CPC ............ *G21K 1/067* (2013.01); *A61B 6/4035* (2013.01); *A61B 6/484* (2013.01); *G02B 5/1866* (2013.01);
(Continued)

(58) Field of Classification Search
CPC .... G21K 1/067; G21K 2207/005; G21K 1/06; A61B 6/4035; A61B 6/484; A61B 6/4291; G02B 5/1866
See application file for complete search history.

(56) References Cited

U.S. PATENT DOCUMENTS

| 8,718,228 B2 | 5/2014 | Nakamura et al. |
| 2007/0183579 A1 | 8/2007 | Baumann et al. |

(Continued)

FOREIGN PATENT DOCUMENTS

| CN | 101013613 A | 8/2007 |
| CN | 101532969 A | 9/2009 |

(Continued)

OTHER PUBLICATIONS

Zhou et al., "Simple equations for the calculation of a multilevel phase grating for Talbot array illumination", Optics Communications 115, 1995, pp. 40-44.
(Continued)

*Primary Examiner* — Courtney Thomas
(74) *Attorney, Agent, or Firm* — Laurence Greenberg; Werner Stemer; Ralph Locher

(57) ABSTRACT

A phase grating for a phase contrast X-ray imaging device has a transverse surface which is to be aligned substantially transversely with respect to a radiation incidence direction and which is spanned by an x-axis and a y-axis perpendicular thereto. The phase grating is formed from a multiplicity of grating webs composed of a basic material, which are arranged alternately with optically denser interspaces. The grating webs subdivide the transverse surface into grating strips which are in each case elongated in the y-direction and which are lined up parallel alongside one another in the x-direction. The phase grating has in each grating strip along a z-axis, which is perpendicular to the transverse plane, a homogeneous total thickness of the basic material which
(Continued)

always differs between adjacent grating strips. At least one grating web extends within the transverse surface over a plurality of grating strips.

11 Claims, 15 Drawing Sheets

(51) Int. Cl.
*G02B 5/18* (2006.01)
*A61B 6/00* (2006.01)

(52) U.S. Cl.
CPC .............. *G21K 1/06* (2013.01); *A61B 6/4291* (2013.01); *G21K 2207/005* (2013.01)

(56) References Cited

U.S. PATENT DOCUMENTS

| | | |
|---|---|---|
| 2009/0092227 A1 | 4/2009 | David et al. |
| 2010/0246764 A1 | 9/2010 | Itoh et al. |
| 2011/0051889 A1 | 3/2011 | Sato |
| 2012/0201349 A1* | 8/2012 | Kaneko ................ A61B 6/4035 378/62 |
| 2014/0112440 A1 | 4/2014 | David et al. |
| 2015/0055744 A1 | 2/2015 | Anton et al. |

FOREIGN PATENT DOCUMENTS

| | | |
|---|---|---|
| CN | 102047344 A | 5/2011 |
| CN | 102626320 A | 8/2012 |
| CN | 102971620 A | 3/2013 |
| EP | 1731099 A1 | 12/2006 |
| WO | 2009113726 A2 | 9/2009 |
| WO | 2014180901 A1 | 11/2014 |

OTHER PUBLICATIONS

Engel et al., "Contrast-to-noise in X-ray differential phase contrast imaging", Nuclear Instruments and Methods in Physics Research A 648, pp. 202-207; 2011.
Weitkamp et al., "X-ray phase imaging with a grating interferometer"; Optics Express, vol. 13, No. 16, published Aug. 8, 2005, pp. 6296-6304; 2005.
Raupach et al.: "Analytical evaluation of the signal and noise propagation in x-ray differential phase-contrast computed tomography", in: Phys. Med. Biol., 2011, vol. 56, pp. 2219-2244, DOI:10.1088/0031-9155/56/7/020.
Suleski Thomas, "Generation of Lohmann images from binary-phase Talbot array illuminators", Applied Optics, vol. 36, No. 20, Jul. 1997, pp. 4686-4691.
Weber et al., Noise in x-ray grating-based phase-contrast imaging, Med. Phys. 38 (7), Am. Assoc. Phys. Med., pp. 4133-4140; 2011.
Szwaykowski et al., "Talbot array illuminator with multilevel phase gratings", Applied Optics, vol. 32, No. 7, Mar. 1993, pp. 1109-1114.
Pfeiffer et al., "Phase retrieval and differential phase-contrast imaging with low-brilliance X-ray sources", Nature Physics, vol. 2, Apr. 2006, pp. 258-261.
Momose, Atsushi, "Recent Advances in X-ray Phase Imaging", Japanese Journal of Applied Physics, vol. 44, No. 9A, 2005, pp. 6355-6367.
Weitkamp,Timm, et al.: "X-ray phase imaging with a grating interferometer", Laboratory for Micro- and Nanotechnology, Paul Scherrer Institut, 5232 Villigen PSI, Switzerland, Aug. 8, 2005 / vol. 13, No. 16 / Optics Express 6304.

* cited by examiner

PHASE CONTRAST X-RAY IMAGING DEVICE AND PHASE GRATING THEREFOR

BACKGROUND OF THE INVENTION

Field of the Invention

The invention relates to a phase contrast X-ray imaging device, in other words to an X-ray device for phase contrast imaging. The invention relates, moreover, to a phase grating therefor. The device and phase grating are provided, in particular, for phase contrast imaging in the medical sector.

The interaction of electromagnetic radiation in general, and X-ray radiation in particular, with a medium is conventionally described by specifying a complex refractive index. Real part and imaginary part of the refractive index are each dependent on the material composition of the medium with which the complex refractive index is associated. Whereas the imaginary part reproduces the absorption of the electromagnetic radiation in the medium, the real part of the refractive index describes the material-dependent phase speed, and therewith the refraction of the electromagnetic radiation.

X-ray imaging devices that are currently used usually detect only the material-dependent radiation absorption in an object to be examined, with the intensity of the X-ray radiation transmitted by the object being recorded in a spatially-resolved manner.

Less common nowadays is the use of the refraction caused by the object and the material-dependent phase shift that accompanies it for the purpose of imaging. Corresponding methods and devices are currently being developed.

A Talbot-Lau interferometer is typically used for metrological detection of the phase shift, as is described, for example, in "X-ray phase imaging with a grating interferometer, T. Weitkamp at al., 8 Aug. 2005/Vol. 13, No. 16/OPTICS EXPRESS".

In the case of the known Talbot-Lau interferometer an X-ray radiation source, a phase grating (or diffraction grating) $G_1$, an analysis grating (or absorption grating) $G_2$ and an X-ray detector constructed from a large number of pixels are arranged along an optical axis. Arranged between the X-ray radiation source and the phase grating is often also a coherence grating $G_0$ which is used for ensuring sufficient spatial coherence in the X-ray radiation. The coherence grating can be omitted if the X-ray radiation source can already innately be considered in a sufficiently good approximation as punctiform.

Generally an optical component is called a phase grating, and this changes the phase position of a radiation beam penetrating it transversely to the direction of propagation of the radiation in a spatially periodic manner, whereby, after passing through the phase grating, the radiation forms an—as a rule strip-like—interference pattern on the analysis grating. The period length of the coherence grating is chosen such that the interference maxima of the light beams emanating in each case from the individual columns of the coherence grating are mapped on each other.

The analysis grating is arranged at a distance $d_{12}$ from the phase grating, which corresponds to one or several times the Talbot distance $d_T$ ($d_{12}=k \cdot d_T$; where k=1, 2, 3, . . . ). The structure of the phase grating is mapped onto the analysis grating hereby by means of the interference pattern generated by the phase grating (if the phase grating is irradiated by a plane wave).

The known phase grating has a uniform striped structure of grating webs comprising an optically comparatively thin basic material (here silicon) and interspaces therebetween. In conventional phase gratings the interspaces are either empty (air-filled) or filled with non-metallic material, such as, for example, photoresist. Since for X-ray radiation the real part of the refractive index is smaller than one in all materials, the interspaces for X-ray radiation—unlike for visible light—always constitute the optically more dense medium compared to the grating webs. The term "optical" is used here and below also within the meaning of "X-ray optical". It also refers therefore to the wave propagation of X-ray radiation.

In the case of the known phase grating, the grating webs with the interspaces therebetween form a structure comprising adjoining grating strips in a transverse surface which is to be aligned transversely to the incidence direction of the X-ray radiation, wherein the basic material in each of these grating strips has a constant thickness (material height h) in the incidence direction of the X-ray radiation which, however, is always different between adjacent grating strips. In the grating strips formed by the grating webs the material height has a positive value. In the grating strips formed by the interspaces the material height regularly has the value zero by contrast.

The conventionally used phase gratings are, as a rule, binary (two-stage) gratings in which all grating webs have an identical (first) material height, and in which all interspaces have an identical (second) material height (in particular h=0). With a grating of this kind the phase position of the incident X-ray radiation is affected by the varying material height such that, after passing through the phase grating (aside from transition effects), the X-ray radiation is divided into exactly two partial beams each with identical, but different among themselves, phase position. The conventionally used phase gratings as a rule generate a phase deviation between the two partial beams, and this corresponds to half or a quarter of the wavelength. Phase gratings of the first-mentioned type are also called π-gratings, phase gratings of the last-mentioned type are also called π/2-gratings.

The intensity distribution of the interference pattern is detected by means of the X-ray detector. The period of the interference pattern caused by the phase grating is typically much smaller than the size of the pixels of the X-ray detector, however, so direct detection of the interference pattern using the X-ray detector is regularly not possible. In order to nevertheless be able to measure the interference pattern the X-ray detector is therefore conventionally connected upstream of the analysis grating, with the aid of which the interference pattern can be sampled by spatial-periodic masking of X-ray radiation. For this purpose the analysis grating is shifted in a plane perpendicular to the optical axis and the structure of the interference pattern. The coherence grating or the phase grating can also be shifted instead of the analysis grating.

For phase contrast imaging the object to be examined is positioned between the X-ray radiation source (and the optionally present coherence grating) on the one hand and the phase grating on the other hand. As an alternative to this the object can also be positioned between the phase grating and the analysis grating. In both cases the object causes a location-dependent, varying phase shift of the X-ray radiation which measurably changes the interference pattern generated by the phase grating. The changed interference pattern is detected in the manner described above by means of the X-ray detector. The location-dependent phase shift is then calculated-back from the measured intensity distribution of the interference pattern.

The image information is either obtained directly from the phase or, alternatively, the image information can also be ascertained from the density (i.e. the integrated phase) or the angular scattering (dark field). Furthermore, the phase contrast image is sometimes offset against the simultaneously obtained absorption contrast image in order to reduce the image noise.

The desired advantage of phase contrast X-ray imaging consists in that, as a rule, structures in the soft tissue (in particular tissue, water and body fat) stand out more strongly from each other in the phase contrast than in the absorption contrast.

However, owing to the require gratings, Talbot-Lau interferometers—depending on the absorption behavior of the gratings—cause either a comparatively strong loss of intensity (and therefore require a high X-ray dose) or comparatively poor visibility of the interference pattern (and therefore poor resolution of the phase contrast scan). Furthermore, owing to the gratings Talbot-Lau interferometers often have comparatively strong chromatic selectivity. The gratings typically only function well in a narrow wavelength range around a specific design wavelength for which the respective grating is configured. Portions of the X-ray radiation with deviating wavelengths (and quantum energies) frequently cannot be used for imaging or reduce the image quality.

There are tight limits on optimization of the optical properties of conventional phase gratings in that complex grating structures often cannot be produced, or at least not with justifiable expenditure.

BRIEF SUMMARY OF THE INVENTION

The invention is based on the object of improving phase contrast X-ray imaging.

In respect of a phase grating for a phase contrast X-ray imaging device this object is achieved according to the claimed invention. In respect of a phase contrast X-ray imaging device this object is achieved according to the claimed invention. Advantageous embodiments and developments of the invention and in part those that are of themselves inventive are presented in the dependent claims and the following description.

The inventive phase grating has a transverse surface which is spanned by an x-axis and a y-axis perpendicular thereto, and which is to be aligned substantially (i.e. exactly or at least approximately) transversely with respect to a radiation incidence direction. The provided radiation incidence direction defines a z-axis of the phase grating which in the envisaged installation position of the phase grating is oriented, in particular, parallel to an optical axis of the X-ray imaging device oriented. The transverse surface can basically be defined here (as a mathematically abstract structure) within the spatial volume taken up by the phase grating at any desired z-position (i.e. position along the z-axis). It is assumed purely by way of example below that the transverse surface is formed by the "leading" end surface of the phase grating, via which the radiation penetrates the phase grating.

The axes introduced above span a Cartesian coordinate system. The directions defined by the orientation (arrow direction) of the x, y and z axes are called the (positive) x, y and z-directions respectively below. The opposite directions in each case are called the (negative) x, y and z-directions respectively. Positions on the x, y and z axes are called x, y, and z-positions respectively.

Analogously to conventional phase gratings, the inventive phase grating also has a large number of grating webs composed of an optically comparatively thin basic material, wherein these grating webs are separated by optically denser interspaces. Per se likewise in the case of conventional phase gratings, the grating webs are embodied in such a way that they subdivide the transverse surface into elongate grating strips which are lined up parallel alongside one another in the x-direction and extend in the y-direction over the entire transverse surface in each case. These grating strips are characterized in that the phase grating in each grating strip has a homogeneous (i.e. the same everywhere) basic material total thickness along the z-axis (and therefore in the incidence direction of the X-ray radiation), although this is always different between adjacent grating strips. As already established in the introduction, the total thickness of the basic material present over a specific point of the transverse surface along the z-axis is also called the "material height". The material height identifies the optical path length of the phase grating at the associated point of the transverse surface.

In contrast to conventional phase gratings, in the inventive phase gratings the surface areas respectively taken up by the grating webs and interspaces within the transverse surface are not congruent with the grating strips, however. In other words, there is no one-to-one association between grating strips on the one hand and grating webs or interspaces on the other hand. Instead, within the transverse surface at least one of the grating webs extends over a plurality of grating strips.

Since the grating webs, due to the interspaces that are to be maintained, must run at least approximately parallel, the grating strip-spanning property compulsorily extends to all grating webs (with the exception of boundary effects, namely any grating webs at the edges of the transverse surface which, owing to their edge position, can extend only over one grating strip). In particular, preferably all grating webs regularly extend over a large number of grating strips, in particular over all grating strips—again aside from boundary effects.

As is known, the idea of designing the grating webs of the phase grating so as to span grating strips enables the construction of grating structures with complex spatial distribution of the material height over the transverse surface, and this could not be produced in a conventional design, or at best with high expenditure. The grating strip-spanning layout of the grating webs means that the grating strips of the inventive phase grating—unlike in the case of conventional phase gratings—are mathematically abstract structures which, as a rule, are not directly mapped by physical structures of the phase grating. The grating strips are instead defined solely by the above-described spatial distribution of the grating height and the optical properties of the phase grating connected therewith. In simple embodiments of the inventive grating the grating strips preferably have a homogeneous (i.e. the same for all grating strips) width in the x-direction. However, within the context of the invention the grating strips can also have different widths. As shown below, such embodiments of the phase grating are even particularly advantageous under certain conditions.

The grating webs are preferably formed from gold, nickel or silicon. The interspaces are optionally formed by (air- or liquid-filled) gaps or by intermediate webs made from an optically comparatively dense solid (i.e. a solid with, for X-ray radiation, a comparatively large real part of the refractive index), e.g. from photo resist.

The phase grating is preferably produced in a photolithographic production process, in particular what is known as the LIGA (lithography-electroplating-molding) process or by means of reactive ion etching.

One limiting factor for production of the phase gratings is the aspect ratio limited by production processes, which with a given grating height in the z-direction is determined by the minimum distances to be maintained between the side walls of the grating webs, namely by the minimum thickness of the grating webs and the minimum thickness of the interspaces.

In an expedient embodiment of the invention the grating webs are designed such that they run within the transverse surface with diagonal (i.e. at an angle to the y-axis that exceeds 0° and falls below 90°) preferred direction over a plurality of grating strips. The preferred direction is formed by the orientation of the grating webs within the transverse surface averaged over a plurality of grating strips. Locally, i.e. within a single grating strip, the grating webs can also run parallel to the x-axis or y-axis. In particular, the grating web running diagonally over the transverse surface with respect to its preferred direction can be composed in a tiered manner of sections which are oriented so as to be alternately parallel to the x-axis or y-axis.

As is known, the above-described diagonal layout of the grating webs with a given grating height and given diffraction characteristics of the grating strips means particularly large minimum distances can be maintained between the side walls of the grating webs—both within the grating webs and between adjacent grating webs. This in turn enables phase gratings with a particularly large grating height in the z-direction, or particularly low width of the grating strips to be produced. Such phase gratings enable phase contrast X-ray imaging devices with particularly short installation length and particularly high sensitivity to be implemented.

In a preferred embodiment the grating webs are each formed in the manner of oblique prisms inclined in the y-direction, the base surface and top surface of which are each located in the end surfaces of the phase grating ($G_1$) parallel to the transverse surface. In this embodiment the phase grating is produced, in particular, by a photolithographic process, in particular LIGA, with angular exposure of the photo resist layer by X-ray radiation. The base surface and the opposing top surface of the prism each have, as a rule, a complex, polygonal form. Within the context of the invention, at the side edges of the phase grating the grating webs can—in contrast to a pure prismatic form—be cut to form edge surfaces oriented in the z-direction.

The grating webs are in particular designed and arranged such that a material structure that repeats itself in the y-direction with a y period length results in each grating strip. The grating webs are therefore designed such that in one grating strip they always take up parallel-shifted, congruent and uniformly spaced-apart surface sections. The grating webs are inclined in the y-direction such that the top surface of each grating web opposing the base surface is offset with respect to the base surface by a whole number of period lengths, in particular exactly one period length. The two opposing end surfaces of the phase grating in the z-direction therefore have an identical layout, i.e. an identical material structure formed from grating webs and interspaces.

The side surfaces of the grating webs, via which the grating webs adjoin the adjacent interspaces, are preferably each alternately formed from first partial surfaces, which are oriented parallel to the y-axis, and second partial surfaces, which are oriented parallel or diagonally to the x-axis. The first and second partial surfaces are preferably each formed by flat (non-curved) surface sections. The second surface sections expediently always extend over a whole number of grating strips within the transverse surface. The transition between first and second partial surfaces of a side surface therefore preferably coincides with the transition between two grating strips in each case.

The above-mentioned diagonal setting of the second partial surfaces of the grating webs against the x-axis is advantageous, especially since comparatively flat angles are produced hereby between first and second partial surfaces of the same grating web, whereby the production-engineering disruption to the grating structure, caused by corner rounding, is kept small. The gradient $g=\Delta y/\Delta x$ in the transverse surface characterizing the setting angle of the grating webs against the x-axis is preferably chosen here such that its absolute value does not exceed 0.5 ($0<|g|\leq 0.5$). This gradient g is also called the "offset gradient" below.

Within the same grating strip all second partial surfaces (i.e. the second partial surfaces of all grating webs which cross this grating strip) expediently run parallel, i.e. in the x-direction, or diagonally with the same offset gradient. Within the context of the invention the second partial surfaces of the grating webs can have different offset gradients in different grating strips, however. Since the offset gradient relates equally here to the two material edges of a grating web in one grating strip it does not change the phase shift encoded in this grating strip.

In one expedient embodiment of the phase grating each grating web runs within the transverse surface with a diagonal preferred direction in the positive y-direction and in the negative y-direction in alternating sections. The grating webs therefore have kinks. The grating webs are preferably bent alternately in opposite directions at regular intervals along the x-axis, so the respective grating web within the transverse surface runs in a meandering manner about the x-axis. The intermediate webs made of photo resist carved out firstly by exposure to X-ray radiation and subsequent development are mechanically stabilized during production of the phase grating in the LIGA process by the layout bent once or several times for the grating webs.

Basically the inventive phase grating can be configured as a binary (two-stage) grating in which the material height jumps alternately back and forth between exactly two values in the x-direction (i.e. with the sequence of the lined up grating strips). The inventive phase grating is preferably designed as a multi-stage grating, however. Here and below the term "multi-stage" is used within the meaning of "more than two-stage" and therefore denotes a phase grating in which the material height varies between at least three values. As is known, particularly favorable optical properties can be achieved with a multi-stage phase grating. A higher value for the product of sensitivity and visibility can therefore be attained for this kind of a phase grating than for conventional binary phase gratings. In particular, the chromatic selectivity of the phase grating can be kept especially low with a multi-stage grating. With a given sensitivity the visibility can firstly therefore be increased by the design of the phase grating described above because the phase grating tolerates polychromatic X-ray radiation better. Secondly, the sensitivity can be increased without impairing the visibility compared to a conventional phase grating. Since the X-ray dose required for achieving a predefined image quality is quadratically connected to the product of sensitivity and visibility, the inventive design of the phase grating enables a significant reduction in the X-ray dose without this having to be accepted by dint of a loss in image quality.

In preferred embodiments of the invention one or more of the above-described embodiment feature(s) is/are attained, moreover, in the phase grating or the phase contrast X-ray imaging device fitted therewith in order to optimize the optical properties of the phase grating:

(1) Reducing the Period of the Coherence Grating:

The phase grating is preferably designed such that (in the case of irradiation by means of a punctiform X-ray radiation source) it generates narrow interference maxima at the level of the analysis grating, the width of which falls below a quarter of the period length $p_2$ of the analysis grating. This enables the period length $p_0$ of the coherence grating to be reduced to a fraction (e.g. to halve, third, etc.) compared to conventional designs. The coherence grating is therefore designed such that the interference maxima of two radiation beams emanating from adjacent columns of the coherence grating to be mapped onto the analysis grating so as to be mutually offset. A corresponding number of further interference maxima are generated hereby between two interference maxima each of a radiation beam. Consequently the number of interference maxima generated per period of the phase grating—also called multiplicity m—is increased. This increases the sensitivity without the width of the spectrum being limited.

For example, the period length $p_0$ of the coherence grating is halved (and this corresponds to a doubling of the multiplicity) compared to the typical construction of a conventional phase contrast X-ray imaging device. The period length $p_2$ of the analysis grating is halved accordingly, whereas the distance $d_{12}$ between the phase grating and the analysis grating is preferably retained. The sensitivity S is doubled hereby and the sensitivity factor f of the phase grating quadrupled.

The phase gratings, which are suitable for this construction, often initially have only e.g. half the sensitivity factor f=k/4 compared to conventional π-gratings (to which f=k/2 applies). Where f=k, by halving $p_0$ and $p_2$ these phase grating attain double the sensitivity factor, however, compared to π-gratings.

Detailed Information:

The strip number of the phase grating per period and the number of interference maxima (with parallel exposure) generated by the phase grating on the analysis grating per period of the phase grating do not have to have common divisors. A phase grating having 7 strips of equal width $p_1/7$ per period length $p_1$ can, for example, cause 2 or 3 interference maxima on the analysis grating per period of the phase grating (as a function of the selected distance $d_{12}$).

Material heights can firstly be determined or designed such that in the distance $d_{12}$ all beams penetrate an x-position with the same phase. With a fixed x-position on the analysis grating this applies to all periods of the phase grating. The more strips there are per grating period, the more this construction resembles a discretized lens. This x-position on the analysis grating can (again with parallel exposure) correspond to e.g. a strip center ("c"="center") or a strip border ("b"="border") on the phase grating. Interestingly, expedient gratings also result with a, in part, greater sensitivity factor f if "a sign error is made" and the phase shifts ΔΦ of each strip are replaced by 2π−ΔΦ. If a grating geometry is available for k=1 it can be expedient to optimize this locally in each case for a change at k>1, to choose strip widths so they are successively different or to adjust phase shifts per strip. These local optimizations are applied in particular to adjust the phase grating to a specifically predefined polychromatic spectrum of the X-ray radiation to be irradiated.

Optimum material heights and strip widths can differ slightly from the analytically ascertained material heights and strip widths, in particular if the distance $d_{12}$ between the phase grating and the analysis grating is a multiple of the Talbot distance (k>1). This can be expedient to better adjust the construction to the specific tube spectrum.

The reduction in the periods of the coherence grating is also possible (and even particularly expedient) if, between the original narrow, but intensive principal maximum of the interference pattern, even further weaker interference maxima occur, although with a reduction in the period of the coherence grating these coincide with the shifted principal maxima (and thereby suddenly make a positive contribution to visibility).

The above-described reduction in the periods of the coherence grating constitutes a stand-alone invention which can basically also advantageously be used in phase contrast X-ray imaging devices with different (not inventive) phase gratings if these phase gratings generate sufficiently narrow interference maxima.

(2) Reduction of Color Errors by Shifting the Phase by Multiples of 2π:

If the material height at specific grating strips is increased or lowered by a height interval $\Delta h=\delta\cdot\lambda_D$ (where δ is a decrement in the complex refractive index of the basic material where n=1−δ+iβ), the phase of a partial beam transmitted through these grating strips is shifted by X-ray radiation of design energy $\lambda_D$ by 2π with respect to a partial beam which passes through a material height that is lower or greater by Δh. Accordingly, the wave front of the partial beam transmitted through the increased grating strip is shifted by a wavelength. This modification leaves the optical properties of the phase grating unchanged at the design energy. However, the grating modified in this way behaves differently at different energies (or wavelengths) of the X-ray radiation.

Since only differences in the material height between the adjacent grating strips count, the material height of all grating strips can always be reduced, so the grating strips with the lowest material height obtain a diminishing material height (h≈0).

For example, it should be assumed that the grating strips of the phase grating have, in a regular sequence, the three material heights $h_0$=0, $h_1$=10 μm and $h_2$=30 μm, and that the height interval Δh has the value 50 μm.

In this case the material height $h_0$ can be increased by the height interval Δh to $h_0$=50 μm. In a further step the material heights $h_0$, $h_1$, $h_2$ um je 10 μm can be reduced, so the material height $h_1$ assumes the value zero: $h_0$=40 μm, $h_1$=0 and $h_2$=20 μm. In a similar manner the material height $h_1$ can be increased in further steps by the height interval Δh to $h_1$=50 μm, and the material heights $h_0$, $h_1$, $h_2$ reduced by 20 μm each, so the material height $h_2$ assumes the value zero: $h_0$=20 μm, $h_1$=30 μm and $h_2$=0. All of the modifications to the grating structure described above can be made here without changing the optical properties of the phase grating at the design wavelength.

With an L-stage phase grating, in which the grating strips of the phase grating L (where L=2, 3, 4, . . . ) have different material heights, L different modifications of the same grating type can be produced in this way. Even with binary phase gratings (where L=2)—although not with π-gratings and π/2-gratings—the modified grating affects X-ray radiation with a wavelength different from the design wavelength in a different way to the original phase grating.

With irradiation of the phase grating with polychromatic X-ray radiation it has sometimes also proven advantageous for the visibility to also inflate the material height of such grating strips, which already originally have a material height that is not zero, by one or several times the height interval Δh.

Exemplary embodiments of the invention will be illustrated in more detail below with reference to drawings, in which:

DESCRIPTION OF THE INVENTION

Figure 1:
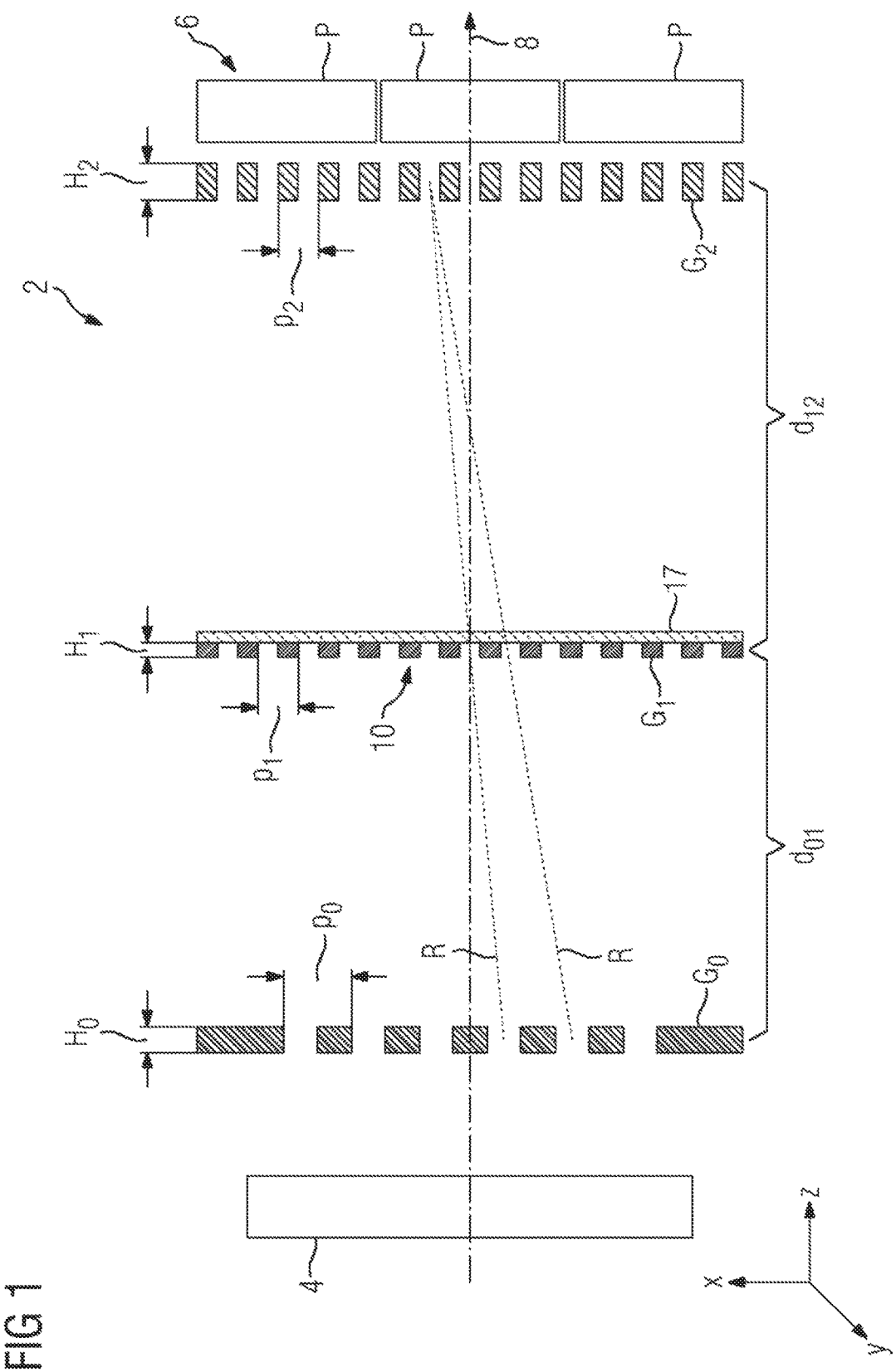
FIG. 1 shows in a roughly schematic sectional view a phase contrast X-ray imaging device having a phase grating.

Mutually corresponding parts, variables and structures are provided with identical reference numerals in all figures.

The (phase contrast X-ray imaging) device 2 schematically shown in FIG. 1 comprises an X-ray source 4, a coherence grating $G_0$, phase grating $G_1$, an analysis grating $G_2$ and an X-ray detector 6 constructed from a large number of pixels P.

An axis z (hereinafter called the z-axis or optical axis 8), which in the case of the exemplary embodiment is oriented in a z-direction, can be associated with the construction. The individual optical elements of the X-ray device 2 are designed so as to be flat in the exemplary embodiment, arranged along this optical axis 8 and oriented perpendicular thereto in each case.

The X-ray device 2 is provided for obtaining medical phase contrast images. For image recording, a patient is positioned between the coherence grating $G_0$ and the phase grating $G_1$, preferably immediately in front of the phase grating $G_1$. Metrological detection, or rather the ascertainment, of the spatial distribution of the phase shift caused by the patient occurs in the X-ray device 2 presented here according to the principle known per se and described, for example, in "X-ray phase imaging with a grating interferometer, T. Weitkamp at al., 8 Aug. 2005/Vol. 13, No. 16/OPTICS EXPRESS".

The coherence grating $G_0$ is used to ensure adequate spatial coherence of the X-ray radiation used for the interferometric scanning methods. It has a grating structure—preferably made of gold—grating webs having a grating height $H_0$ (measured in the z-direction), and slits arranged between the grating webs, wherein the grating webs and slits extend parallel to an axis y (also called the y-axis)—perpendicular to the axis z and oriented perpendicularly out of the drawing plane of FIG. 1. In the direction of an axis x (also called the x-axis)—again perpendicular to the axes z and y—the grating webs and slits of the coherence grating $G_0$ form a periodic structure having a grating constant (period length) $p_0$. The coherence grating $G_0$ is typically-positioned at a distance of about 10 cm from the X-ray source 4.

In an alternative embodiment of the device 2, instead of a spatially expanded X-ray radiation source 4, a, in a good approximation, punctiform X-ray radiation source is used which emits the already sufficiently coherent X-ray radiation. In this case the coherence grating $G_0$ is omitted.

During operation of device 2 the X-ray radiation source 4 emits X-ray radiation with a photon energy up to about 100 keV.

The phase grating $G_1$ (indicated only roughly schematically in FIG. 1) is arranged offset to coherence grating $G_0$ at a distance $d_{01}$ in the z-direction. This is used, as in a conventional Talbot-Lau interferometer, to generate a strip-like interference pattern, wherein the (interference) strips of this interference pattern extend parallel to each other in the y-direction. As is only roughly indicated in FIG. 1 by broken lines, in the standard development of device 2 the grating constant $p_0$ of the coherence grating is dimensioned such that interference maxima of partial beams R, which issue from adjacent columns of the coherence grating $G_0$, are mapped onto each other.

The phase grating $G_1$ (described in more detail below) has a grating height $H_1$ and, to generate the interference pattern, a strip-like periodic variation in the optical path length in the x-direction with a grating constant (period length) $p_1$.

The analysis grating $G_2$ is positioned offset to the phase grating $G_1$ at a distance $d_{12}$ in the z-direction and has a grating height $H_2$ measured in the z-direction and a grating constant (period length) $p_2$. The analysis grating $G_2$, like the coherence grating $G_0$, consists of strip-like grating webs made of gold and strip-like interspaces formed therebetween.

In the exemplary embodiment according to FIG. 1 the extents of the grating $G_1$ and $G_2$ in the x-direction and in the y-direction are substantially the same. In contrast to the schematic view according to FIG. 1 the extent of the analysis grating $G_2$ in the x-direction and in the y-direction actually substantially matches the extent of the X-ray detector 6, more precisely the detector surface spanned by the pixels P of the X-ray detector 6.

The geometry of the phase grating $G_1$ is characterized by three axes x, y and z which in the normal orientation of the phase grating $G_1$ in the device 2 coincide with the axes x, y and z of the device 2 introduced above. Normally the phase grating $G_1$ is therefore arranged within the framework of the device 2 such that its axis z is arranged parallel to the optical axis 8, and therefore to the averaged radiation propagating direction of the device 2. The axes x and y of the phase grating $G_1$ span a transverse surface 10 that extends perpendicular to the radiation incidence direction. As mentioned above, by way of example, the end surface of the phase grating $G_1$ is identified by the transverse surface 10 that faces the X-ray source 4 and at which the X-ray radiation therefore penetrates the phase grating $G_1$.

Figure 2:
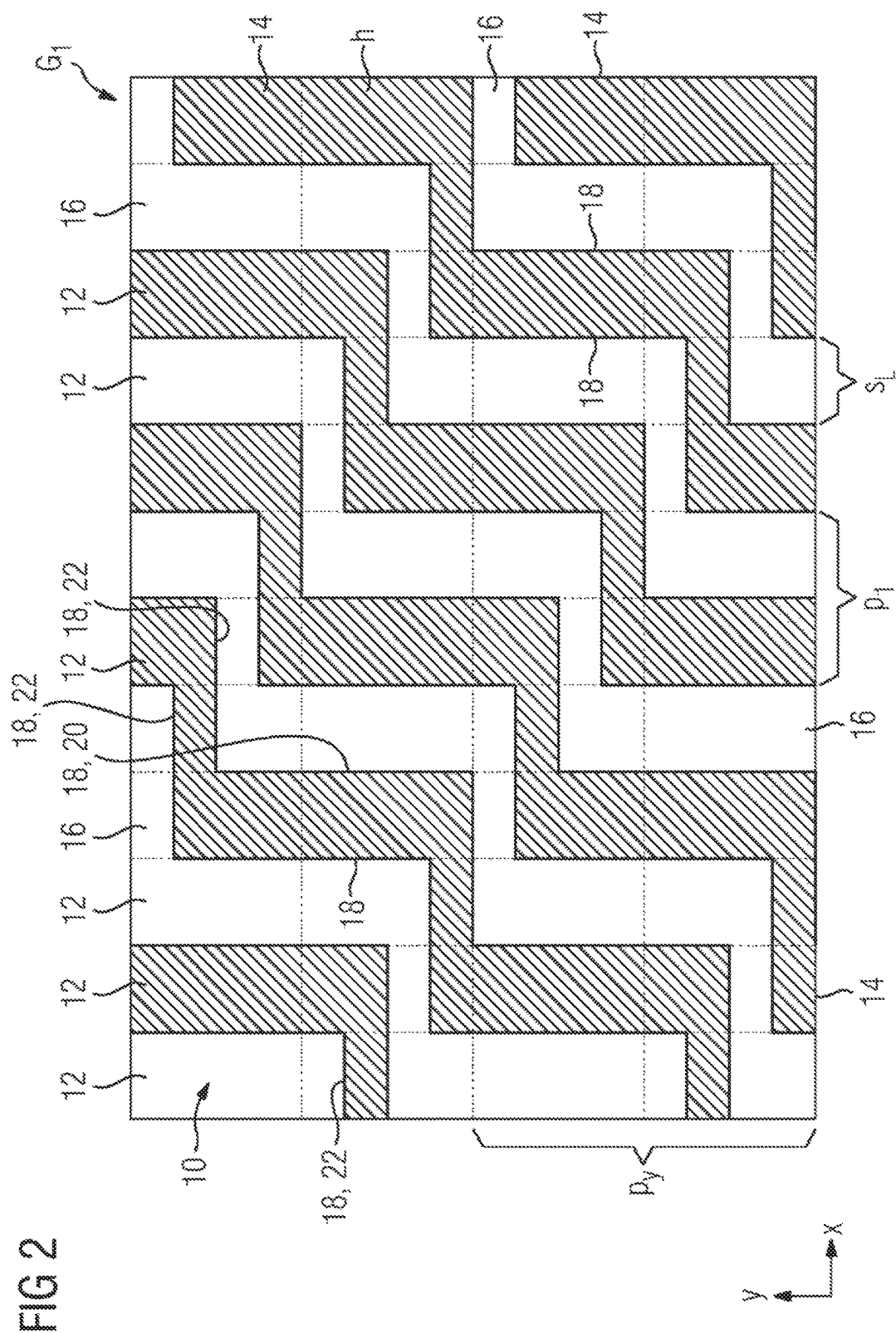
FIG. 2 shows in a schematic view of a transverse surface a detail of a layout for the phase grating, wherein the transverse surface is traversed by diagonally running grating webs composed of a basic material and interspaces arranged therebetween, and wherein the transverse surface is subdivided into a number of parallel grating strips, wherein in each grating strip the phase grating in the radiation propagating direction has a constant, but different between adjacent grating strips, total thickness (material height) of basic material.

In accordance with grating constant $p_1$ the transverse surface 10, of which a detail is shown in greater detail in FIG. 2, of the phase grating $G_1$ is subdivided into individual elongate grating strips 12 (FIG. 2) which each extend in the y-direction over the entire transverse surface 10 and are lined up parallel alongside one another in the x-direction.

To influence the phase position of the irradiated X-ray radiation the phase grating $G_1$ is formed from a number of approximately parallel grating webs 14 composed of a basic material (e.g. nickel, silicon or gold), between which interspaces 16 are formed. The interspaces 16 are air-filled gaps. Alternatively, the interspaces 16 can, however, also be filled by intermediate webs made of photoresist. The grating webs 14 and the optionally present intermediate webs are constructed on a base plate 17 (FIG. 1) of the phase grating $G_1$ which is oriented parallel to the transverse surface 10 and in the example according to FIG. 1 forms, by way of example, the back (remote from the X-ray source 4) end surface of the phase grating $G_1$.

The phase grating $G_1$ is preferably produced by means of the LIGA process. For this purpose a radiation-absorbing mask (e.g. made of gold) is positioned over a photoresist layer applied to the base plate 17 and exposed to X-ray radiation (exposure radiation). As a result of subsequent development, fill areas in the form of holes or trenches are excavated from the photoresist layer and these form a negative mold for the grating webs 14 that are to be produced. In a subsequent electroplating process step these fill areas are filled with the basic material. Following production of the grating webs 14 the photoresist remaining in the interspaces 16 can be left to form intermediate webs or be excavated to form the gaps.

The structure of the mask used in the LIGA process matches the material structure which is visible on the transverse surface 10 of the finished phase grating $G_1$. A detail of one example of this material structure (hereinafter also called a layout) is shown in FIG. 2. The grating webs 14 (corresponding to the gold structures of the mask) are shown as hatched areas here. The corresponding interspaces 16 (to the gaps in the mask) are shown as white areas.

The grating strips 12 of the phase grating $G_1$ are defined in that the phase grating $G_1$ has the same basic material total thickness everywhere in the region of every grating strip 12 (i.e. over each point of the region of the transverse surface 10 delimited from the grating strip 12) in the z-direction (optionally in total over a plurality of material sections). This total thickness is hereinafter also called the material height h associated with the respective grating strip 12. The material height h is always different between different grating strips by contrast. The material height h (understood as the mathematical function of the x and y-positions within the transverse surface 10) rapidly changes value at the transition between two adjacent grating strips 12 therefore. Correlated with the material height h is the optical path which each partial beam of the incident X-ray radiation covers within the phase grating $G_1$, and therefore the phase position of the respective partial beam on exiting the phase grating $G_1$. Due to the periodic variation in the material height h in the x-direction, with grating constant $p_1$ the phase grating therefore generates a periodic modification in the phase of the X-ray radiation likewise in the x-direction. The interference-generating grating effect of the phase grating $G_1$ is based on this.

As can be seen from FIG. 2, the area respectively taken up by every grating web 14 within the transverse surface 10 is not congruent with one of the grating strips 12. In particular, the grating webs 14 and the interspaces 16 therebetween do not run consistently in the y-direction. Instead, the grating webs 14 and the interspaces 16 therebetween extend over the transverse surface 10 with a diagonal preferred direction. Apart from some boundary effects (i.e. cut partial volumes at the edges of the phase grating $G_1$), all grating webs 14 have the same form. Similarly, apart from some boundary effects (i.e. cut partial volumes at the edges of the phase grating $G_1$), all interspaces 16 also have the same form. In the exemplary embodiment according to FIG. 1 the grating webs 14 and interspaces 16 are arranged so as to be shifted parallel to each other in the y-direction within transverse surface 10, so the material structure in the transverse surface 10 has a periodicity with a period length $p_y$. This above-described embodiment of the grating webs 14 is also called a "diagonal layout" below.

The two side surfaces 18, by which each grating web 14 is delimited from the adjacent interspace 16, are subdivided by a sequence of first partial surfaces 20 which are oriented in the y-direction, and second partial surfaces 22 which, in the exemplary embodiment according to FIG. 2, are oriented in the x-direction.

In each of the side surfaces 18 the first partial surfaces 20 and second partial surfaces 22 follow each other alternately. The second partial surfaces 22 extend over the full width of a whole number of grating strips 12 in each case, so the first partial surfaces 20 always run along the boundaries between two grating strips 12.

The phase grating $G_1$ is produced in the LIGA process under off-axis exposure (angle of exposure $\alpha=15°$). The mask is exposed to exposure radiation whose beam path is oriented in the yz plane.

In the three-dimensional space the grating webs 14 each have the form of a(n) (oblique) prism inclined in the y-direction. Apart from boundary effects (i.e. cut partial volumes at the edges of the phase grating $G_1$), the grating webs 14 therefore have in the transverse plane 10 and the end surface of the phase grating $G_1$ opposing this in the z-direction—corresponding to the base surface and top surface of a prism—parallel, congruent and polygonal surface sections which are shifted relative to each other in the y-direction. The edges of the side surfaces 18 are inclined in the yz plane by an angle corresponding to the angle of incidence of exposure radiation. This inclination is matched to the grating height $H_1$ such that the edges of the side surfaces 18 extend over exactly one period length $p_y$ in the y-direction. An identical material structure exactly overlapping (aligning) in the viewing direction along the z-axis is produced as a result in the transverse surface 10 and the opposing end surface of the phase grating $G_1$. This therefore ensures that the material height h is always constant in each grating strip 12.

In the simple embodiment according to FIG. 2 the phase grating $G_1$ is designed as a merely binary grating in which the material height h in the x-direction periodically changes between just two discrete values. In this embodiment the grating strips 12 of the phase grating $G_1$ have, moreover, a uniform strip width $s_L$, so the strip width $s_L$ corresponds to half the grating constant $p_x$ ($s_L=0.5 \cdot p_x$).

In suitable dimensioning the phase grating $G_1$ according to FIG. 2 has a grating height $H_1=30.29$ μm, a grating constant $p_x=4.00$ μm (and accordingly a strip width $s_L=2.00$ μm). The period length $p_y$ is 8.12 μm. Nickel is provided here as the basic material for the grating webs 14. The interspaces 16 are filled with air. The material height h changes periodically at the transition between adjacent grating strips 12 in each case between 26.56 μm (87.7%·$H_1$) and 3.73 μm (12.3%·$H_1$). In a construction for design energy of the X-ray radiation of 62 keV the phase grating $G_1$ dimensioned in this way acts as a π-grating. Partial beams of the X-ray radiation, which pass through adjacent grating strips of the phase grating $G_1$, therefore leave the phase grating $G_1$ with a path difference of half a wavelength (corresponding to a phase difference of the amount π).

Figure 3:
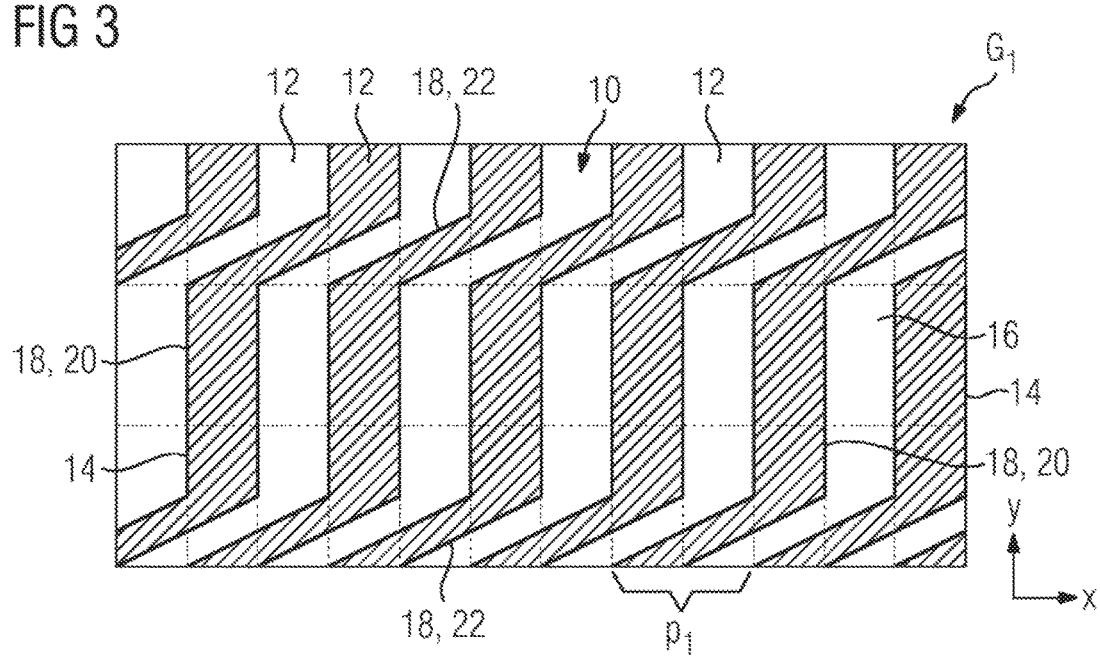
FIG. 3 to 17 show, in a view according to FIG. 2, alternative layouts for the phase grating.

FIG. 3 shows a variant of the above-described grating layout. Unless described otherwise below—with respect to the construction and optical properties, the phase grating $G_1$ shown in FIG. 3 resembles the embodiment according to FIG. 2. In particular, the variant according to FIG. 3 is also a binary π-grating for a design energy of 62 keV. In contrast to the embodiment according to FIG. 2, in the phase grating $G_1$ according to FIG. 3 the second partial surfaces 22 of the side surfaces 18 of the grating webs 14 are not oriented parallel to the x-axis, but set obliquely (with an offset gradient of $g=0.5·\Delta y/\Delta x$) to the x-axis, whereby the intermediate angle between the first partial surfaces 20 and second partial surfaces 22 and the corner rounding due to production engineering are reduced in the region of this intermediate angle.

Since all second partial surfaces 22 (at least within a grating strip 12) are set up in the same way against the x-axis, and run parallel to each other therefore, the inclined position of the second partial surfaces 22 leaves the optical properties of the phase grating $G_1$ (in particular the phase differences caused by the phase grating $G_1$) unaffected.

Figure 4:
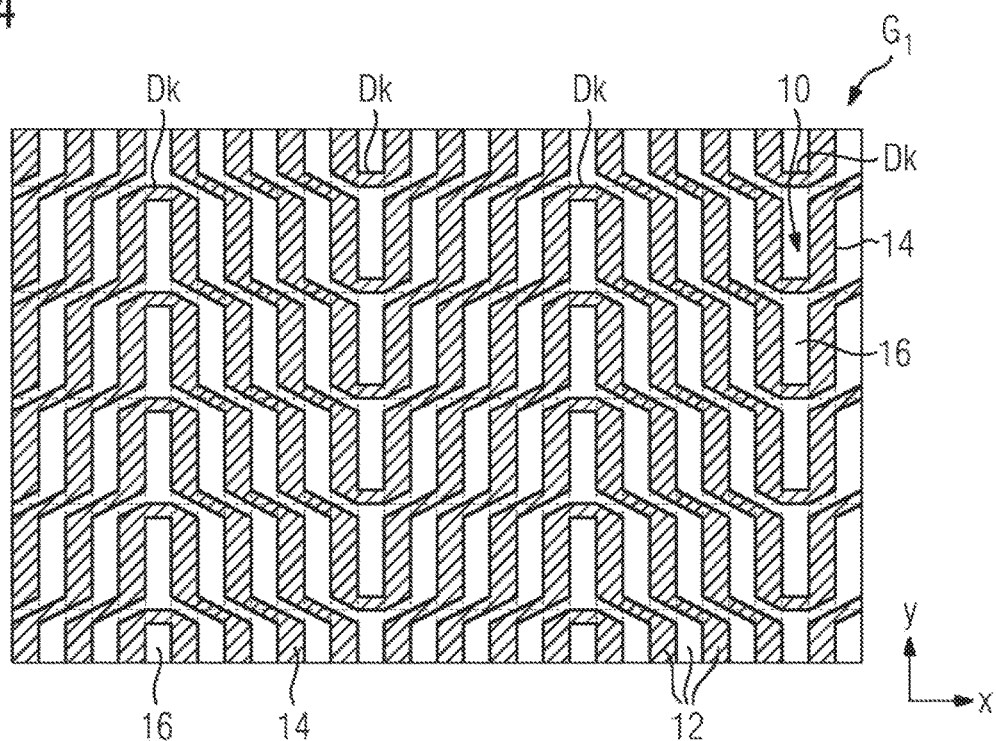
Figure 5:
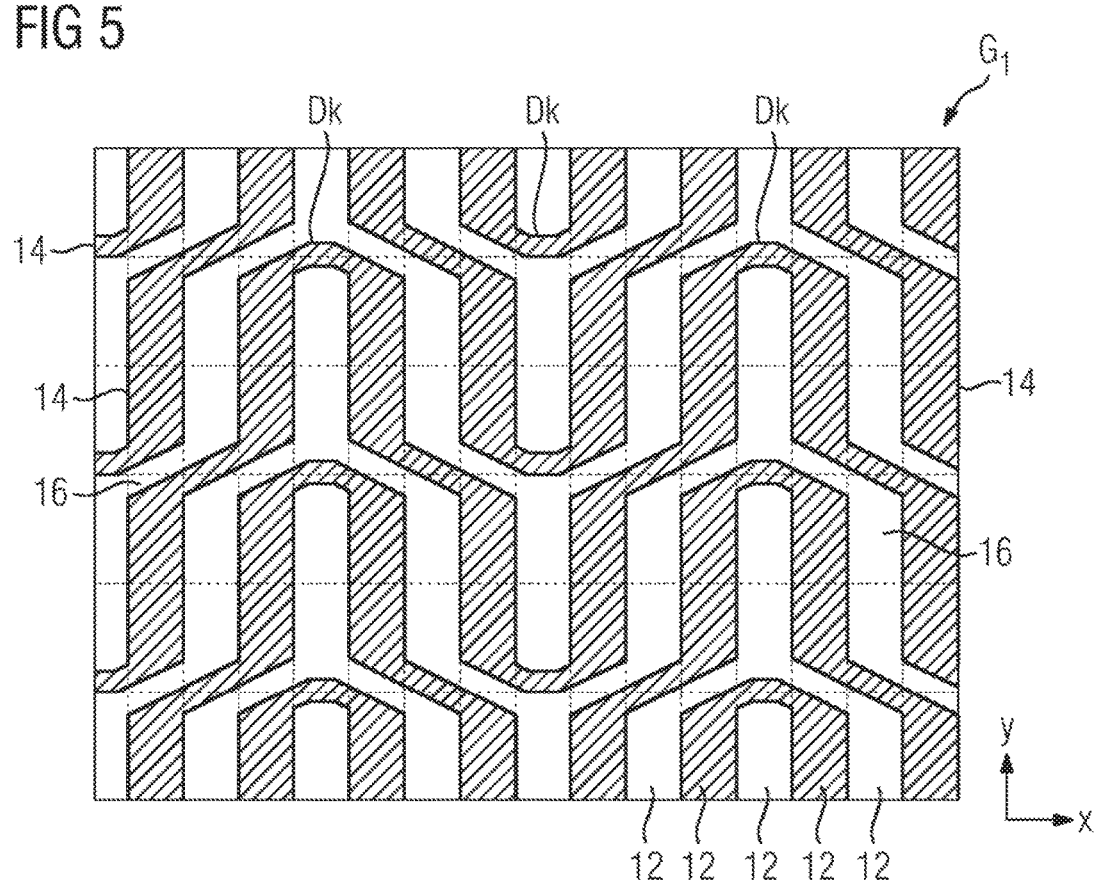
Figure 6:
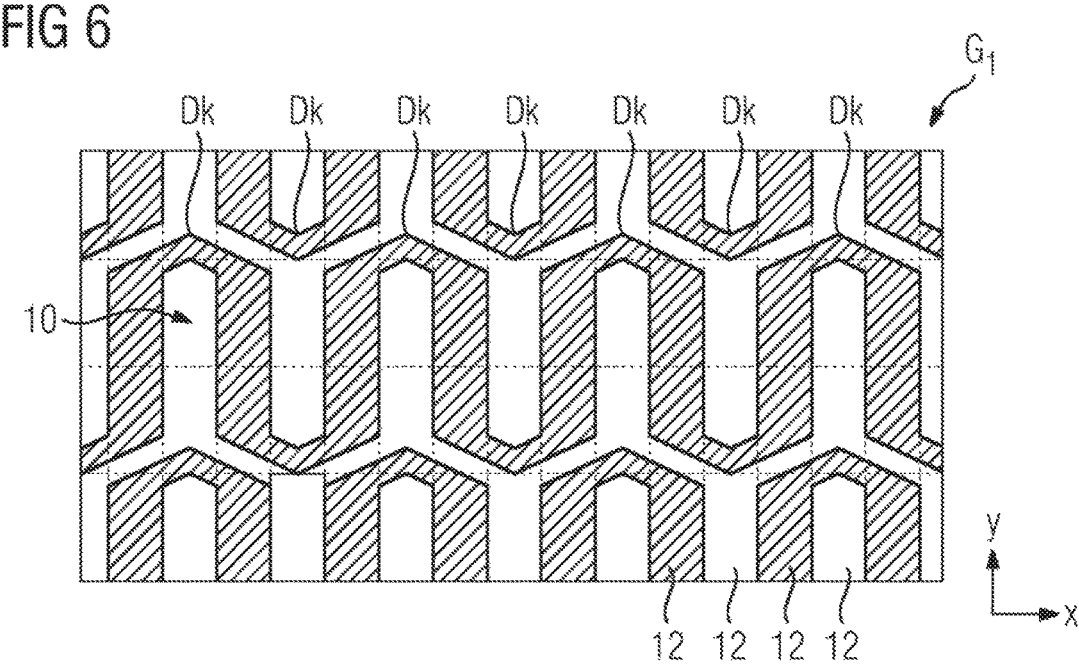

FIG. 4 to 6 show variants of the phase grating $G_1$ according to FIG. 3 again with corresponding optical properties, but in which, in contrast to FIG. 3, kinks DK are provided (with differing frequency) in the diagonal layout, so the grating webs 14 in the transverse plane 10 meander about the x-axis and alternately in certain sections therefore run diagonally in the positive y-direction and in the negative y-direction. The grating webs 14 are advantageously stabilized by the kinks.

Simulation Results for Specific Embodiments of the Phase Grating $G_1$:

With reference to the embodiments of the phase grating $G_1$ illustrated below it will be shown that the above-described construction of the phase grating $G_1$ is advantageous for a reduction in the X-ray dose with phase contrast X-ray imaging, allows a comparatively simple embodiment of grating structures with improved efficiency η in relation to this construction.

The optical properties of the grating $G_1$ in device 2 according to FIG. 1 were ascertained by simulation in each case for these embodiments of the phase grating $G_1$.

Fixed values of 1,000 mm and 200 mm were assumed ($d_{01}=1,000$ mm; $d_{12}=200$ mm) for the distances $d_{01}$ and $d_{12}$. The grating constants $p_0$, $p_1$ and $p_2$ were changed in the individual simulations. In particular, the sensitivity S is proportional to the square root of the sensitivity factor f hereby. In part a duty cycle of 30% was assumed for the coherence grating $G_0$. Corresponding simulations are identified by the designation "V30". In part a duty cycle of 50% was alternatively assumed for the coherence grating $G_0$. Corresponding simulations are identified by the designation "V50". A punctiform radiation source was assumed as a further alternative. These simulations are identified by the designation "V0".

A tungsten anode and an X-ray voltage of 100 kVp (peak kilovoltage) were always assumed for the X-ray source 4 for the simulation. In part the unfiltered X-ray spectrum, divided into 3 keV steps, formed the basis of the simulations. These simulations are identified by the suffix "U". In part filtering of the irradiated X-ray radiation by way of a 200 μm rhenium (Re) filter, followed by a 20 μm Gold (Au) filter was assumed. These simulations are identified by the suffix "F". The spectrum of the filtered radiation was likewise divided into 3 keV steps.

The designation "V50F" therefore denotes a simulation which was based on filtered X-ray radiation and a duty cycle of 50% for the coherence grating $G_0$.

It was assumed for the simulation that the X-ray detector 6 is a quantum counting detector.

Design energy of the X-ray radiation of 62 keV was always assumed.

For a structured development of complex grating structures for the phase grating $G_1$, the phase deviations of the partial beams of the X-ray radiation penetrating the transverse surface 10 required to attain a desired interference pattern at the design energy was calculated by means of modular whole-number arithmetic (mod N where N=2, 3, 4, . . . ). In this connection it transpired that particularly simple, regular phase deviation sequences result for N=4, 8 and 14. Accordingly, the transverse surface 10 of the layout to be generated was firstly subdivided into parallel layout strips oriented in the y-direction, of which a group of 4, 8 or 14 layout strips respectively extends in the x-direction over one or two grating period(s) $p_1$—depending on the desired diffraction properties of the layout. The layouts are provided below with the basic designation "%4", "%8" or "%14" according to the value of the divisor N assumed in their calculation.

A calculated phase deviation was associated with each of these layout strips, and this was then converted into a corresponding material height h for the layout.

The layout strips are not necessarily identical to the grating strips 12 of the finished layout. Instead, a plurality of adjacent layout strips can be provided with the same phase deviation and therefore forms a shared grating strip 12.

Depending on whether the respective embodiment of the phase grating $G_1$ generates the interference maxima (in a projection along the z-axis) so as to be centered with respect to a layout strip or between two layout strips, the above basic designation of the phase grating $G_1$ is followed by one of the letters "c" (for "center") or "b" (for "border").

If a plurality of interference maxima is generated—intrinsically or due to a reduction in the grating constant $p_0$—per grating period $p_1$ by the phase grating $G_1$, this plurality is noted in the grating or simulation designation following the letter "c" or "b" by the abbreviation "x2" (for 2 interference maxima per grating period $p_1$), "x3" (for 3 interference maxima per grating period $p_1$), etc.

Information on the value of the sensitivity factor f of the phase grating $G_1$ in a single Talbot distance follows this in the grating or simulation designation, e.g. 1.00 (for f=1.00 at $d_{12}=d_T$).

If the phase grating $G_1$ is used in multiples of the Talbot distance this is indicated by an abbreviation "x2" (for $d_{12}=2·d_T$), "x3" (for $d_{12}=3·d_T$), etc. again placed at the end. It should be taken into account in this connection that with complex phase gratings $G_1$ the distance $d_{12}$ can also have an odd-number relationship with the Talbot distance, e.g.

"x0.57" (for $d_{12}=0.57 \cdot d_T$). The actual sensitivity factor f results from the product of the value indicated for a single Talbot distance and the distance $d_{12}$ in relation to the Talbot distance. $f=1.00 \cdot 3=3$ therefore follows from the information "1.00x3".

If the phase grating $G_1$ is multi-stage the number of stages is noted by an abbreviation "L3" (for a three-stage grating), "L4" for a four-stage grating), etc. Binary gratings can optionally be denoted in this case by the abbreviation "L2". As a rule, the information on the number of stages is omitted in the designation of binary gratings, however.

The exemplary grating or simulation designation "%8cx2_1.00x3_L3" characterizes the phase grating $G_1$ designated in this way, and therefore the simulation carried out therewith, to the extent that the phase grating $G_1$ has a layout formed from a periodic sequence of eight layout strips each with a constant material height h (%8),
generates two strip-centered interference maxima (cx2) per grating period $p_1$,
has a sensitivity factor k=1.00 for a single Talbot distance, was simulated for three times the Talbot distance, from which an actual sensitivity factor of $k=1.00 \cdot 3=3.00$ results, and
is three-stage (L3), i.e. fluctuates between three different levels of the material height h.

To implement clear designations sometimes further suffixes, e.g. "inv", "inv-100", "inv-200" or "adj-100" are added to the designations construed in this way, and these identify different modifications of the same grating type.

FIG. 7 to 17 show, as illustrated below, selected layouts, for which the optical properties of the phase grating $G_1$ have been simulated. The properties of the respective layout follow in detail [in] TAB 1.1 and TAB 1.2 (Annex 1). The boundary conditions of the respective simulation are laid down in detail in TAB 2.1 (Annex 2). The performance data of the layouts obtained from the simulation are summarized in TAB 3.1 to TAB 3.3 (Annex 3).

Figure 7:
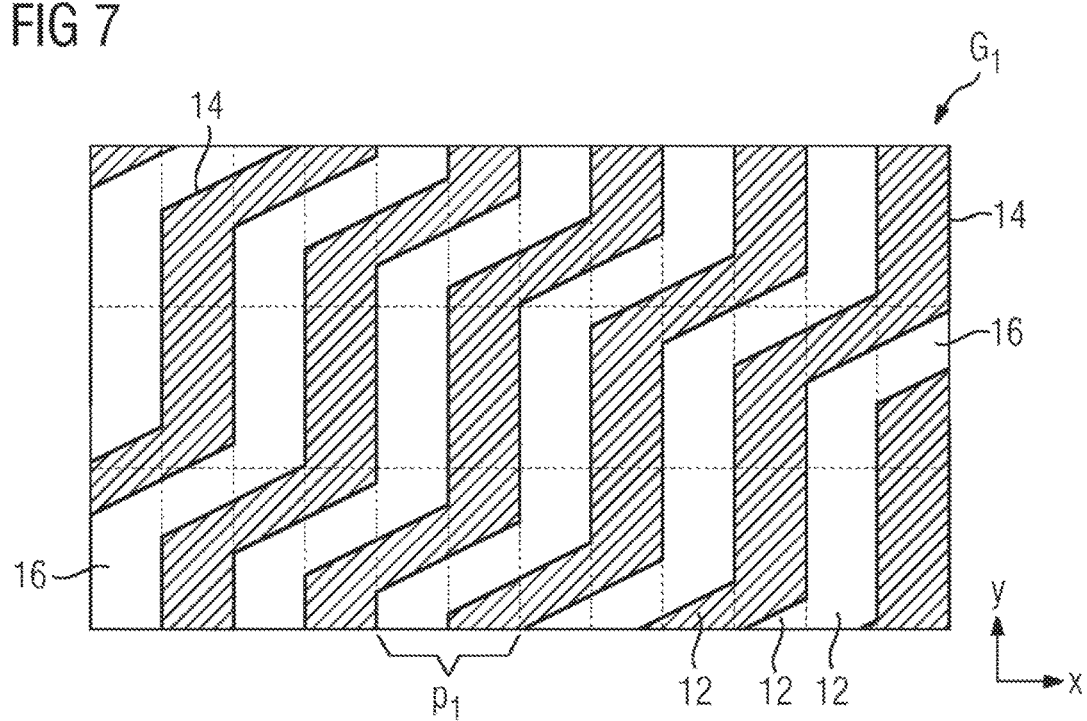

The layout of the phase grating $G_1$ shown in FIG. 7 is based on the simulation designated "%4c_0.50". The phase grating $G_1$ is a binary π/2-grating here.

Figure 8:
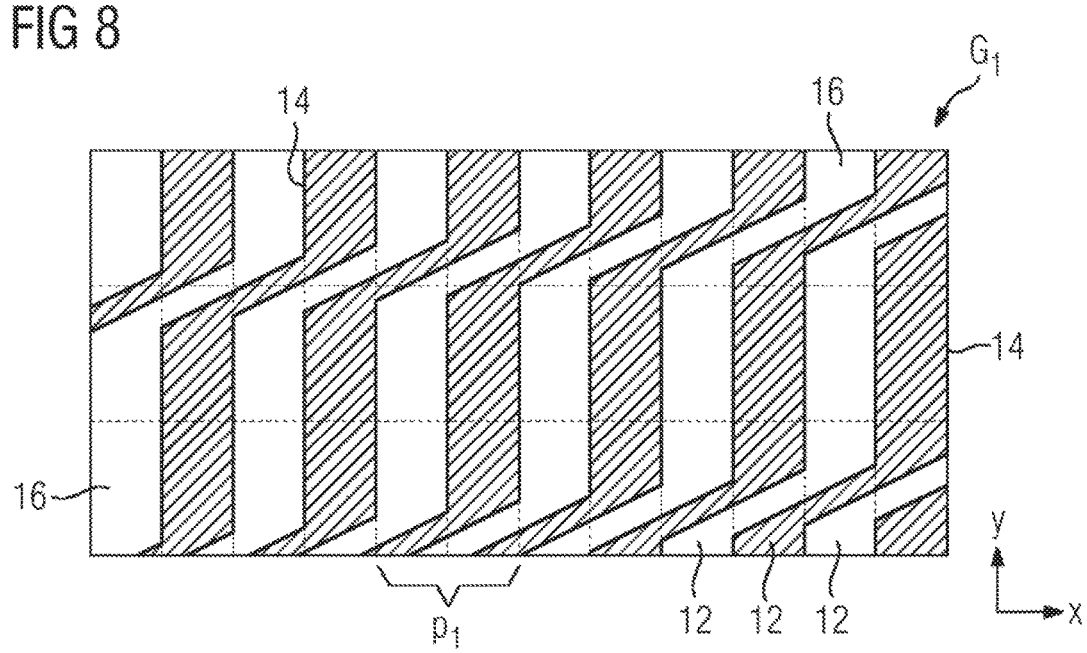

The layout of the phase grating $G_1$ shown in FIG. 8 is based on the simulations designated "%4cx2_0.50", "%4cx2_0.50x3", "%4cx2_0.50x5", "%4cx2_0.50x7" and "%4cx2_0.50x9". The phase grating $G_1$ is a binary π-grating here.

Figure 9:
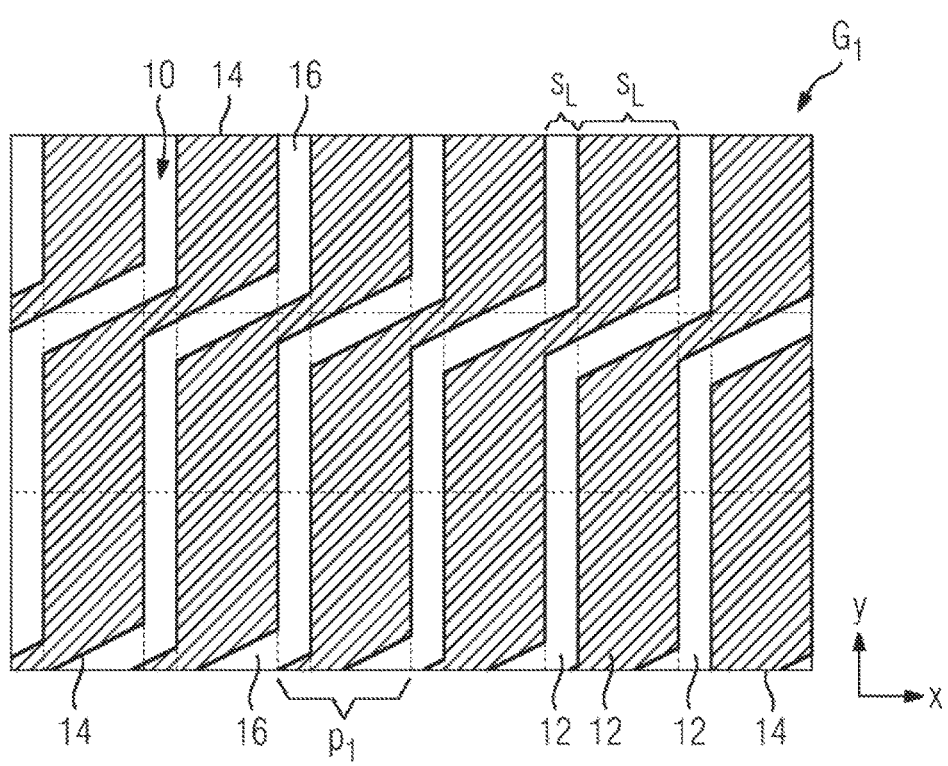

The layout of the phase grating $G_1$ shown in FIG. 9 is based on the simulation designated "%8c_0.25_L2" and "%8cx2_1.00_L2". The phase grating $G_1$ is likewise a binary grating here in which adjacent grating strips 12 have a different strip width $s_L$, however.

Figure 10:
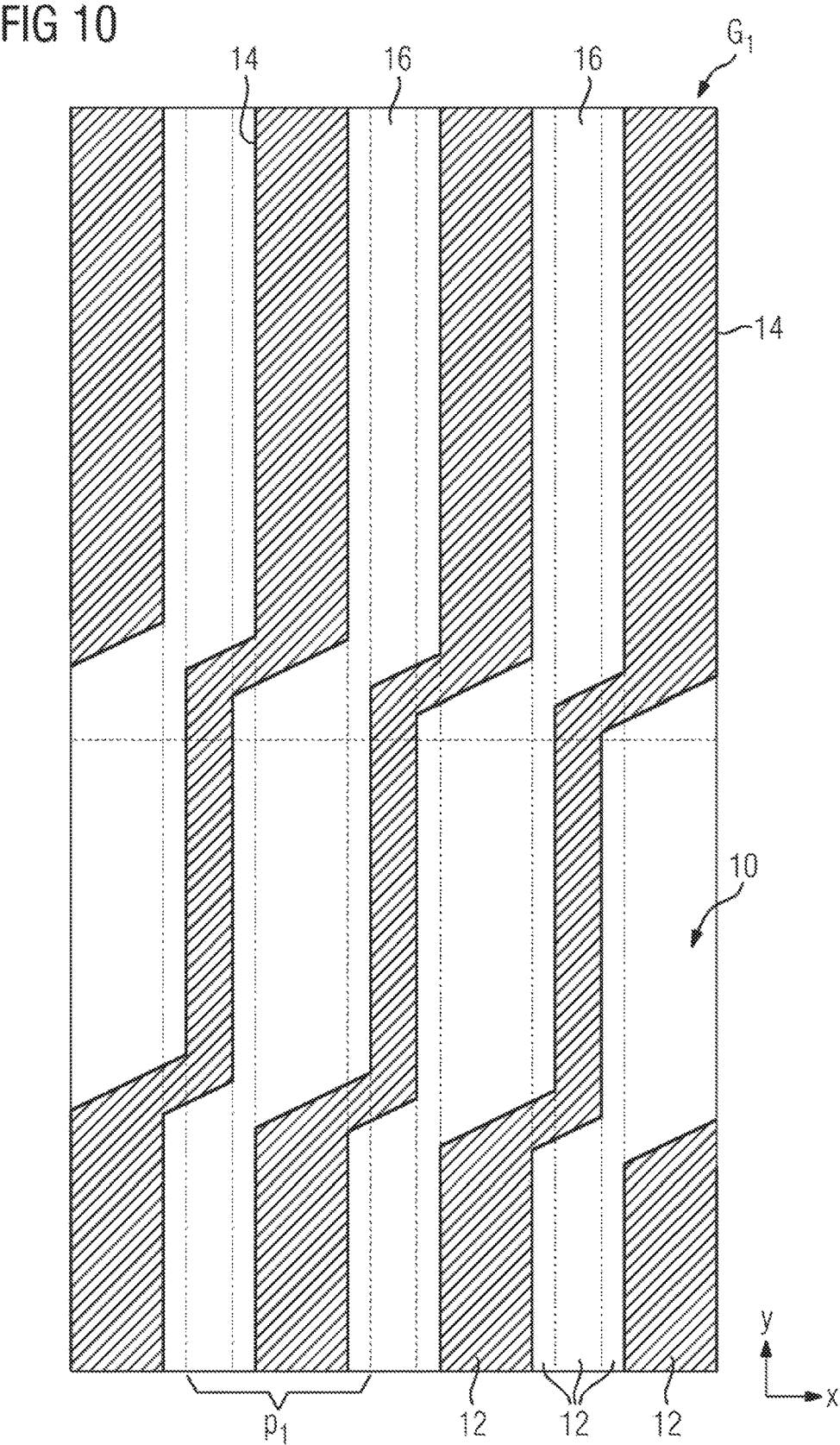
Figure 11:
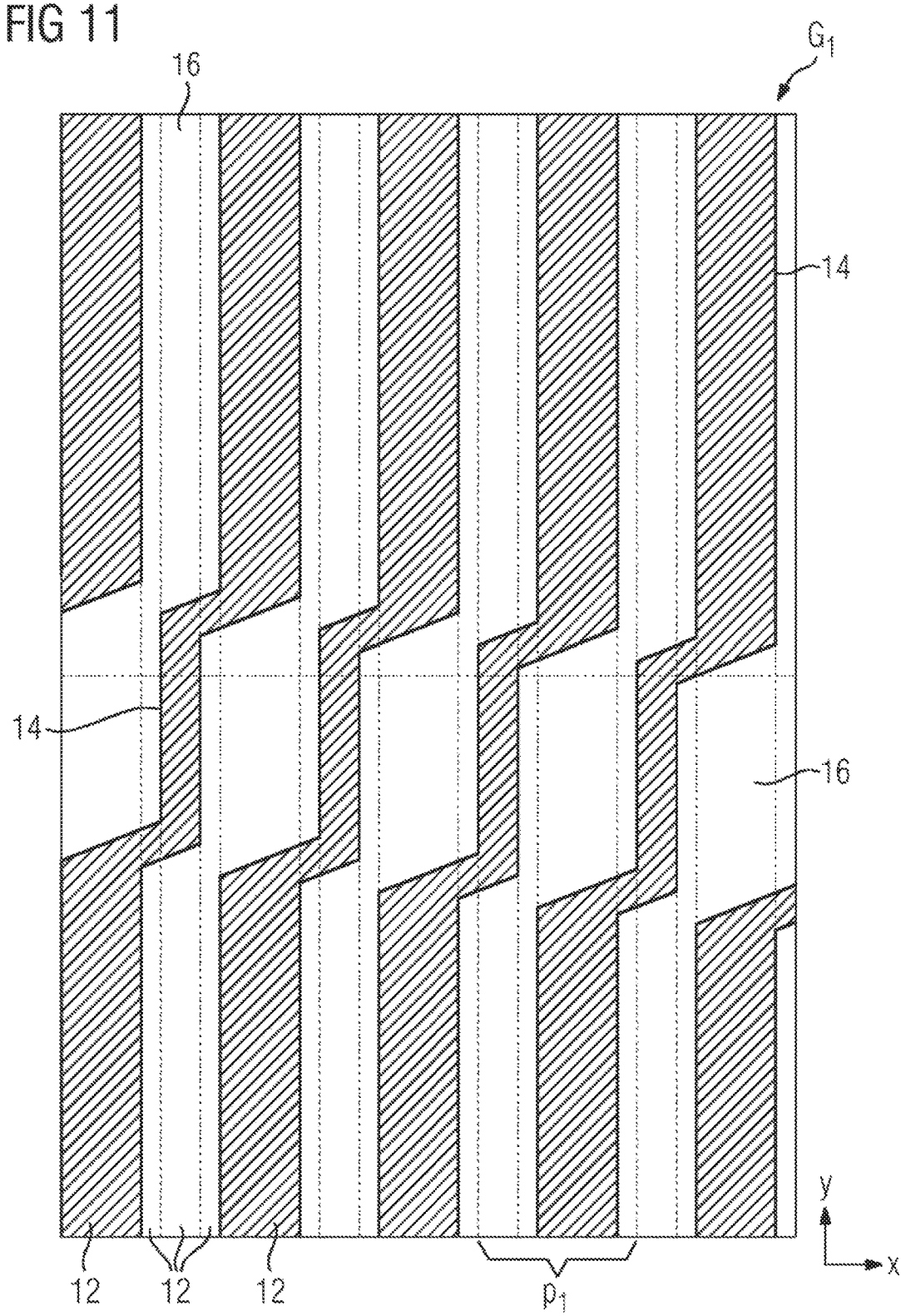
Figure 12:
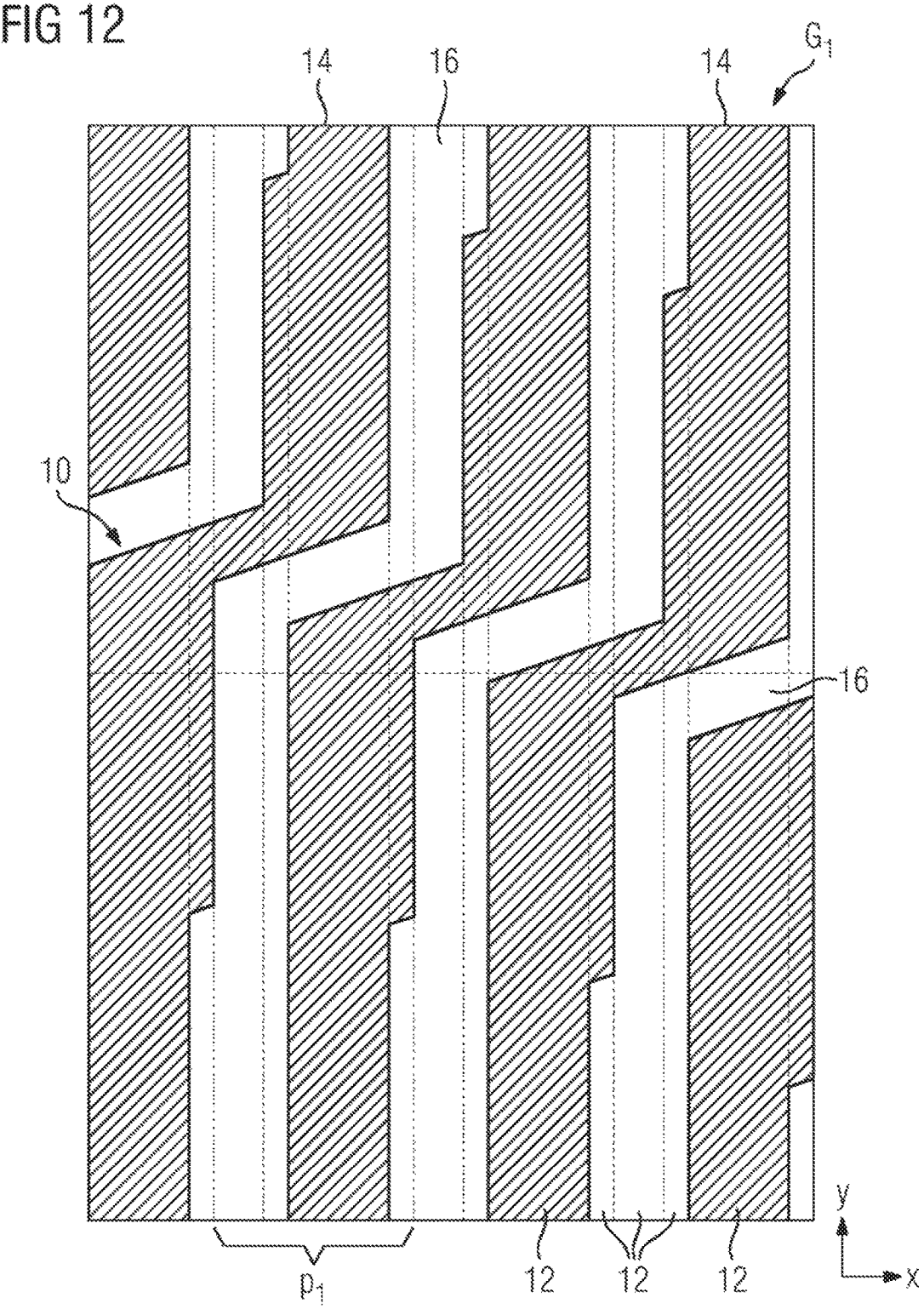

The layouts of the phase grating $G_1$ shown in FIG. 10 to 12 are based on the simulations designated "%8cx2_1.00x3_L3_inv-100" or "%8cx2_1.00x3_L3_inv-200" or "%8cx2_1.00x3_L3_adj-100". The layouts illustrated in the FIG. 10 to 12 correspond to three modifications of the same grating type (i.e. phase gratings $G_1$ with identical optical properties at the design wavelength $\lambda_D$).

All three layouts each reproduce a three-stage grating produced from eight layout strips (four layout strips each per grating period $p_1$), wherein the individual modifications are derived from each other by increasing or lowering the material height h in individual grating strips 12 by a height interval of $\Delta h=\delta \cdot \lambda_D$ and an equal increase in the material height h in all grating strips 12.

Specifically, the layout according to FIG. 10 ("%8cx2_1.00x3_L3_inv100") per grating period $p_1$ is produced from four layout strips with the phase deviation sequence $(1,0,2,0)/2 \cdot 2\pi$ and widths of $(2,1,4,1)/8 \cdot p_1$ (see TAB 1.1 in Annex 1).

The layout according to FIG. 11 ("%8cx2_1.00x3_L3_inv-200") is derived from the layout according to FIG. 10 ("%8cx2_1.00x3_L3_inv-100") by increasing the material height h of the third layout strip (here identical to the third grating strip 12 of the layout in each case), resulting in a phase deviation that is increased by 2π. The phase deviation sequence therefore changes from (1,0, 2,0)/2·2π to (1,0,4,0)/2·2π (cf. TAB 1.1 in Annex 1).

The layout according to FIG. 12 ("%8cx2_1.00x3_L3_adj-100") is again derived as follows from the layout according to FIG. 11 ("%8cx2_1.00x3_L3_inv-200"):

In a first step firstly the material height h of all layout strips and grating strips 12) is mathematically uniformly increased, resulting in a phase deviation that is increased by π. The phase sequence (1,0,4,0)/2·2π therefore migrates to (2,1,5,1)/2·2π.

In a second step the material height h of the first and third layout strips (corresponding to the first and third grating strips 12 respectively) are then mathematically reduced, resulting in a phase deviation reduced by 2π. The phase deviation sequence (2,1,5,1)/2·2π therefore migrates to (0,1,3,1)/2·2π (cf. TAB 1.1 in Annex 1).

As illustrated above, the optical properties of the phase grating $G_1$ at design wavelength $\lambda_D$ remain unaffected by these modifications of the layout.

Figure 13:
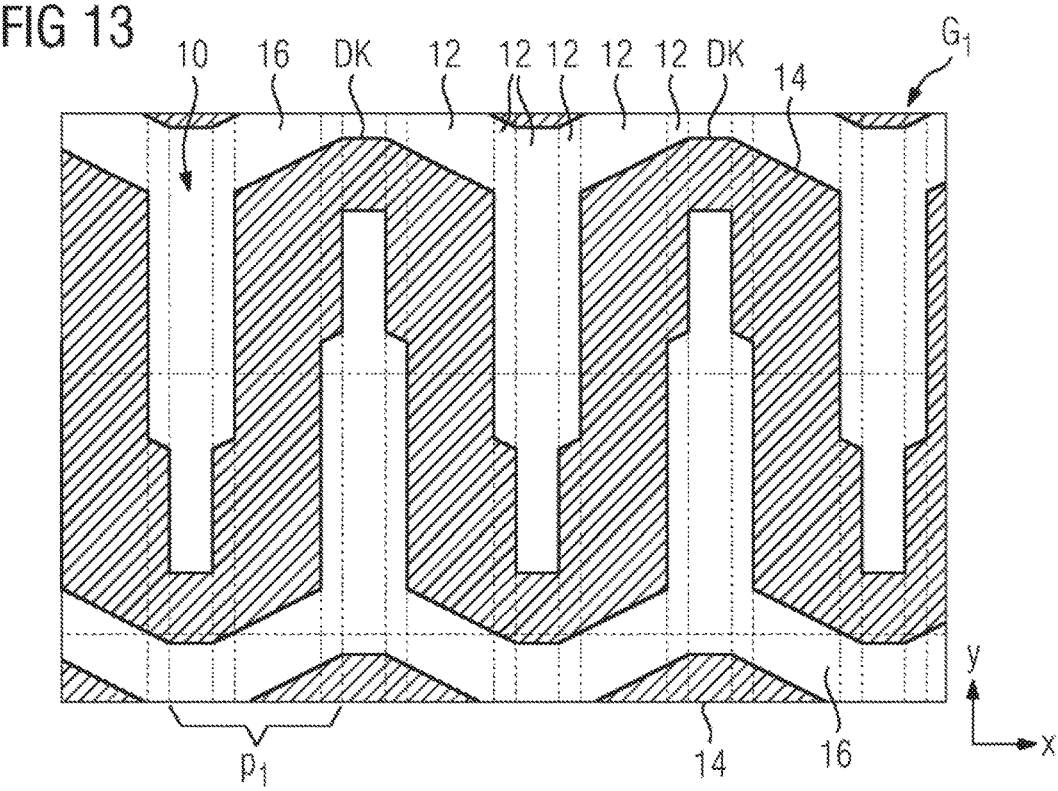
Figure 14:
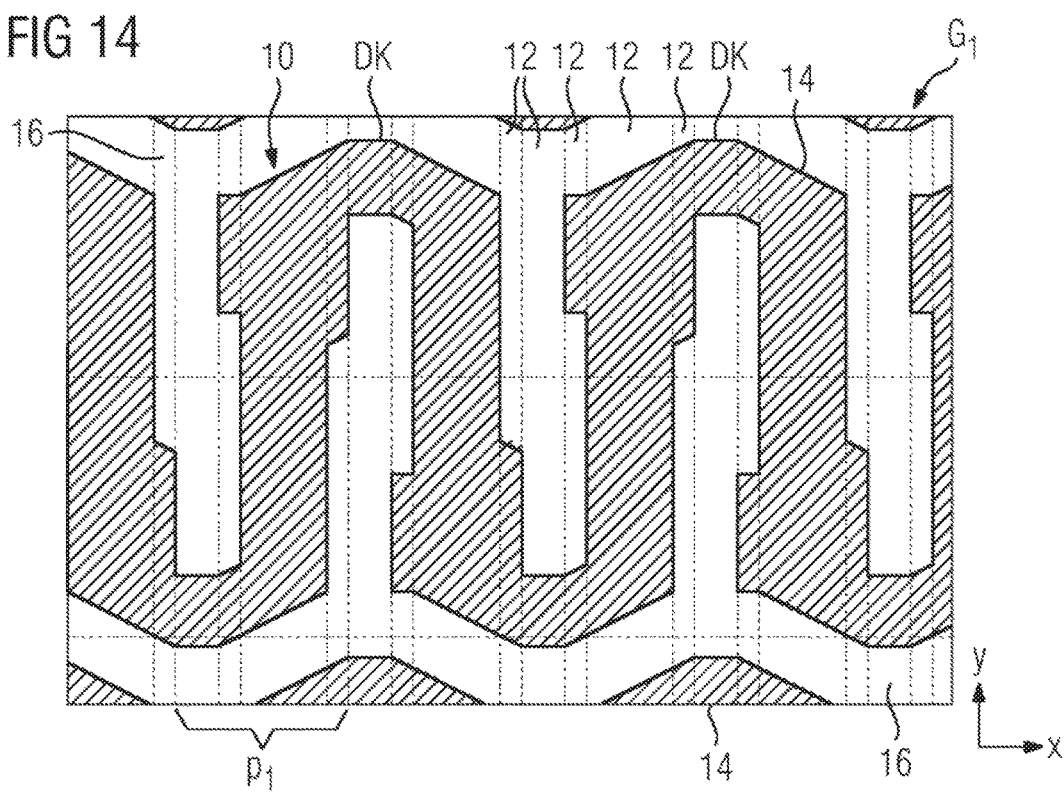

FIGS. 13 and 14 illustrate are variants of the layout according to FIG. 12 ("%8cx2_1.00x3_L3_adj-100") in which the grating webs 14 are provided with kinks DK. With respect to the phase deviations of the successive grating strips 12 and optical properties of the phase grating $G_1$, the layouts according to FIGS. 13 and 14 are identical to the layout according to FIG. 12.

Figure 15:
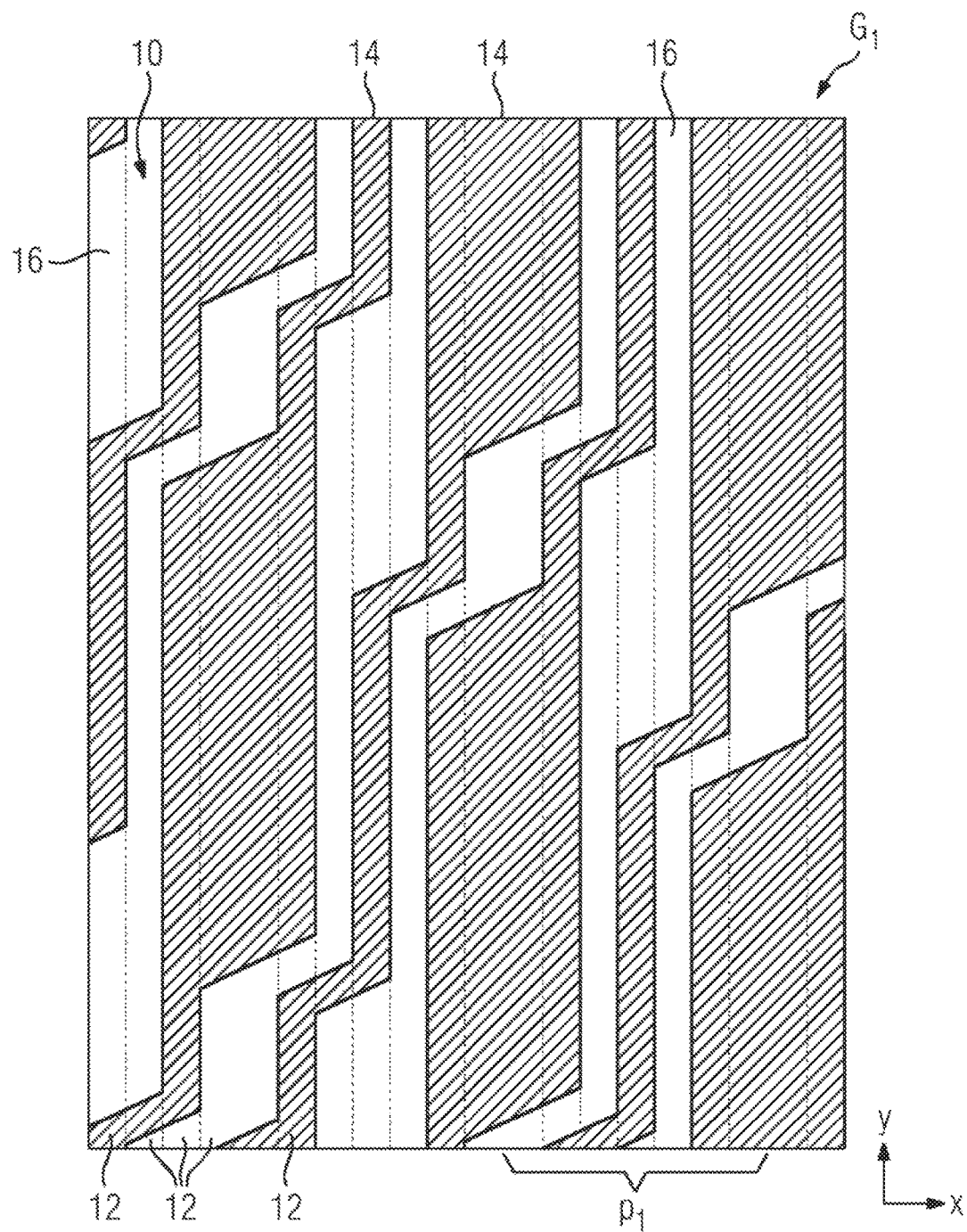

The layout of the phase grating $G_1$ shown in FIG. 15 is based on the simulations designated "%14b_0.14_L4_inv", "%14bx2_0.57_L4_inv" and "%14bx2_1.29_L4_inv".

Figure 16:
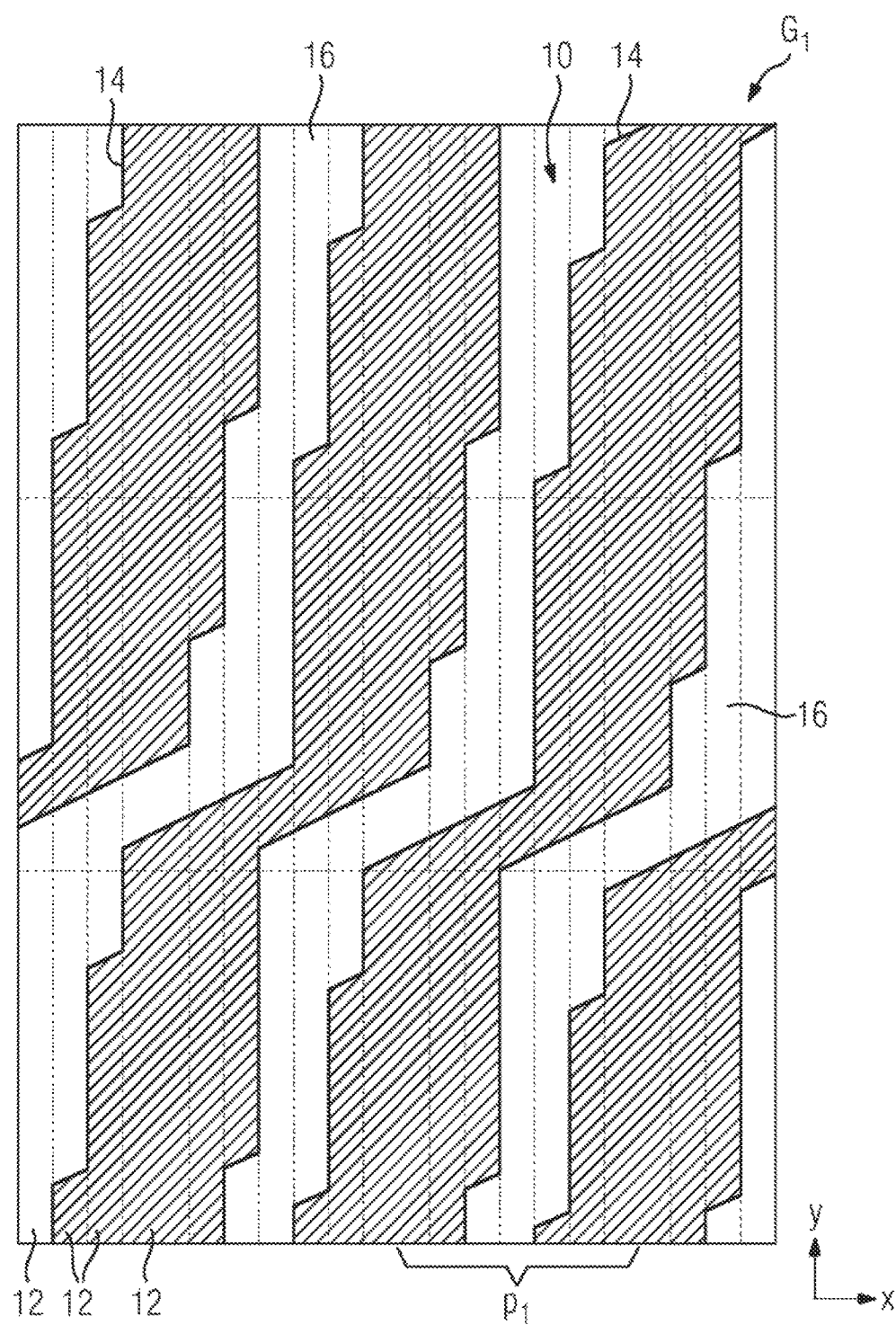
Figure 17:
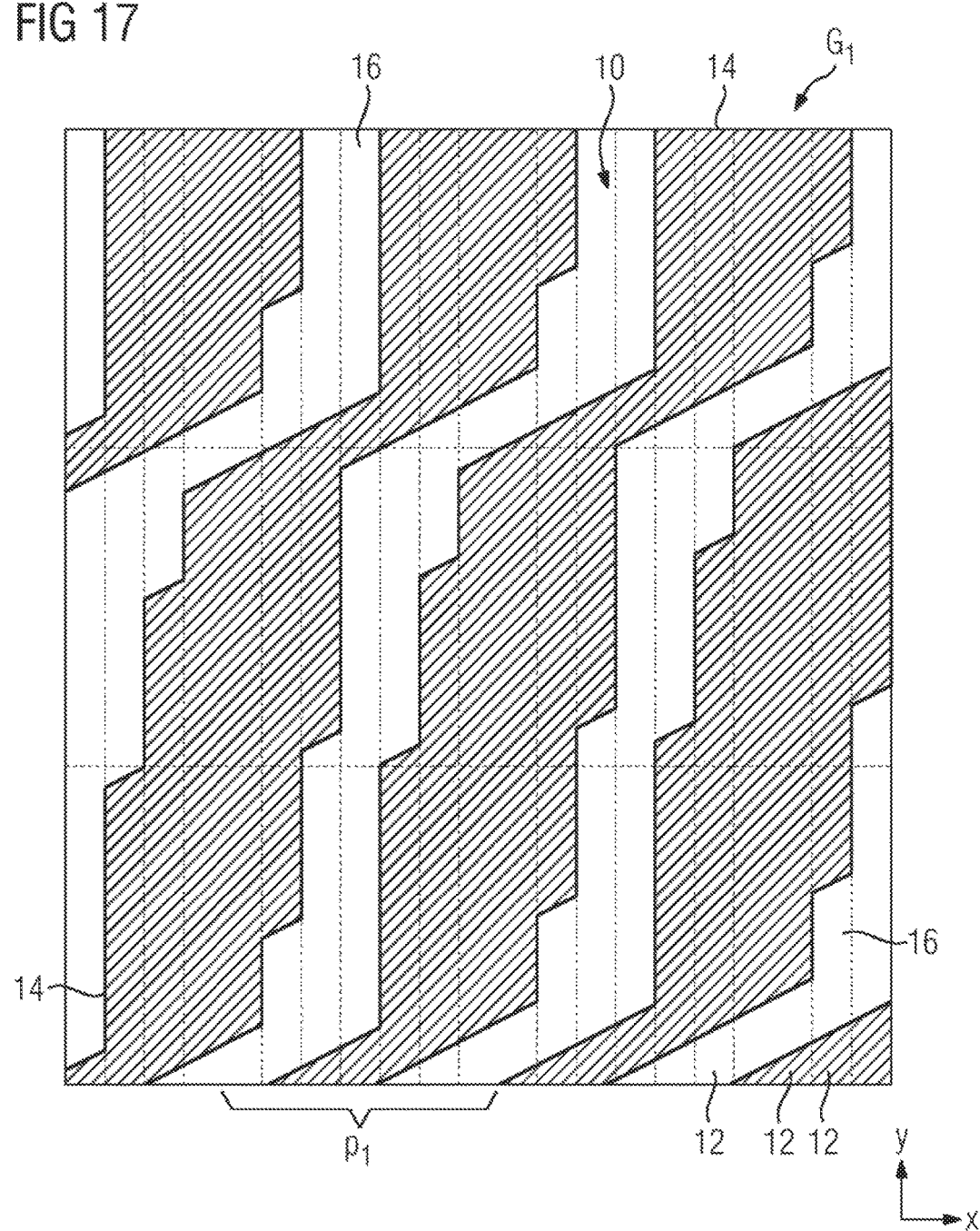

The layouts shown in FIGS. 16 and 17 are based on the simulations designated "%14bx2_0.57x2.5_L4" and "%14bx3_1.29x1.33_L4" respectively.

Figure 18:
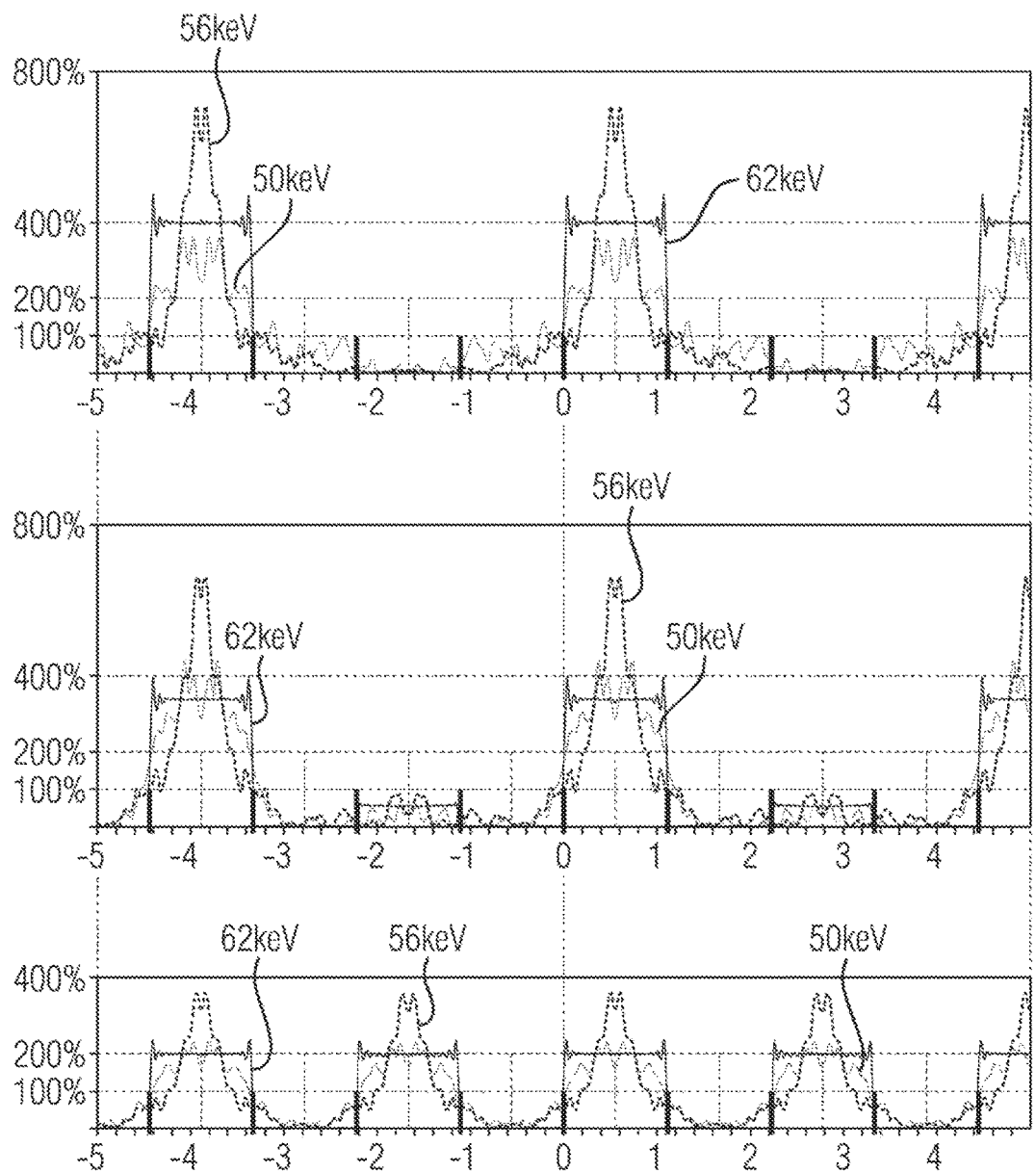
FIG. 18 shows in three graphs, arranged on above the other, of the X-ray intensity over the y-axis the interference pattern of the phase grating according to FIG. 9 (middle graph) and a three-stage comparison grating (top graph) and for the phase grating according to FIG. 9 the interference pattern with halved grating period of the coherence grating (bottom graph)

The top graph in FIG. 18 shows an interference pattern of a three-stage phase grating $G_1$ which has a phase deviation sequence of the successive grating strips 12 of $(0,1,4,1)/8 \cdot 2\pi$ per grating period $p_1$. The intensity characteristic of the X-ray radiation diffracted by the phase grating $G_1$ in the x-direction is specifically shown here, as results from a simulation "%8c_0.25_L3". Plotted are the intensity characteristic for the design energy 62 keV (solid line), and for deviating quantum energies of the X-ray radiation of 56 keV (broken line) and 50 keV (dotted line). In the same view the middle graph in FIG. 18 shows the interference pattern which results for a simulation "%8c_0.25_L2" having a binary comparison grating (such as in "%8cx2_1.00_L2", but where $p_0$=21.9 μm).

According to the top graph in FIG. 18, at the design energy the three-stage grating ("%8c_0.25_L3") illuminates a strip having a width corresponding to a quarter of the grating constant $p_2$ of the analysis grating $G_2$. The center between the interference maxima is relatively dark. For deviating quantum energies the interference maximum is significantly expanded, however. "Shoulders" of the polychromatic intensity profile therefore form close to the interference maximum.

According to the middle graph of FIG. 18, the interference pattern of the simplified binary grating ("%8c_0.25_L2") exhibits an even weaker secondary maximum in the center between the intensive interference maxima. In return the regions between the main and secondary maxima are darker than in the upper graph though (the interference maxima have narrower "shoulders" in other words).

If the binary grating is illuminated by a coherence grating $G_0$ with half the grating constant $p_0$ ("%8cx2_1.00_L2"), the interference pattern shown in the bottom graph of FIG. 18 results, and this is characterized by a halved $p_2$ period. Main and secondary maxima of the diffracted partial beams R issuing from the coherence grating $G_0$ alternately overlap in this interference pattern, whereby good visibility and arrow "shoulders" of the polychromatic intensity are achieved.

If this grating is sampled in three times the Talbot distance (instead of in one times the Talbot distance according to "%8cx2_1.00_L2"), the average visibility is significantly reduced. However, it is clear that a correction is possible by adding material to the width of $p_1/2$, and this generates a phase deviation of $-2\pi$ or $-4\pi$. This trick is surprisingly successful (see TAB 3.1 to 3.3).

While the layouts according to FIG. 10 ("%8cx2_1.00x3_L3_inv-100") and 11 ("%8cx2_1.00x3_L3_inv-200") created in this way have a structure that is relatively difficult to produce by off-axis exposure (for which reason gold is preferably used here as the basic material instead of nickel, causing a lower transmission and therefore a lower output), the modified layout according to FIG. 12 ("%8cx2_1.00x3_L3_adj-100") enables comparatively simple production of the phase grating $G_1$. The angle of exposure for the layout according to FIG. 12 was reduced to 12° for illustrative reasons. For the layouts according to FIGS. 13 and 14 the angle of exposure was reduced further to 4°.

At three times the Talbot distance the layouts according to FIG. 12 to 14 ("%8cx2_1.00x3_L3_adj-100") have a sensitivity which a $\pi$-sliding grating would have at six times the distance. At the same time the layouts according to FIG. 12 to 14 have a visibility, however, which a $\pi$-sliding grating reaches at three times the distance. The layouts according to FIG. 12 to 14 can consequently keep pace with a $\pi$-sliding grating or significantly exceed it even when the latter is used in nine times the Talbot distance.

Figure 19:
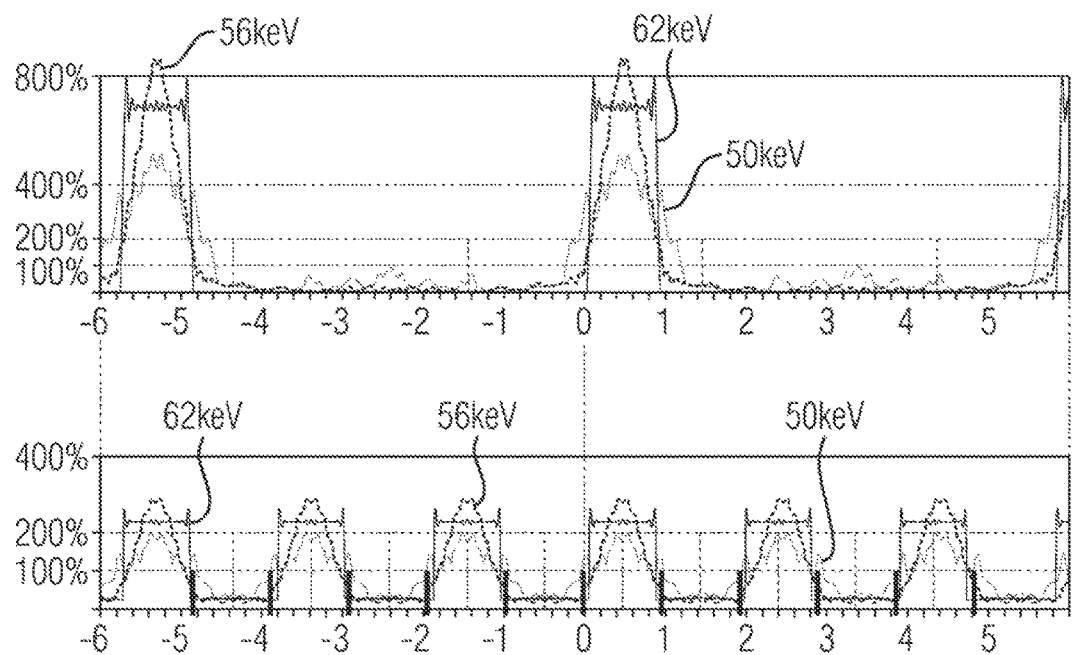
FIG. 19 shows in two graphs, arranged one above the other, according to FIG. 18 the interference pattern of the phase grating according to FIG. 15 in the case of standard grating constants of the coherence grating (top graph) and in the case of thirded grating constants of the coherence grating (bottom graph)

The top graph in FIG. 19 shows—analogously to the graphs in FIG. 18—the interference pattern which was obtained from the simulation "%14b_0.14_L4_inv" for the layout according to FIG. 15 when $p_0=29.0$ μm is considered. For the same layout the bottom graph in FIG. 19 shows the interference patter which was obtained from the simulation "%14bx3_1.29_L4_inv" for a grating constant $p_0=9.7$ μm reduced to a third.

The graphs show that the phase grating $G_1$ produced according to the layout "%14b_0.14_L4_inv" focuses the interference maxima onto a narrow strip whose width corresponds to one seventh of the grating constant $p_2$, so halving or even thirding the grating constant $p_0$ is possible. Halving the grating constant $p_0$ ("%14bx2_0.57_L4_inv") is suggested by weak secondary maxima which can be seen in the top graph of FIG. 19.

Figure 20:
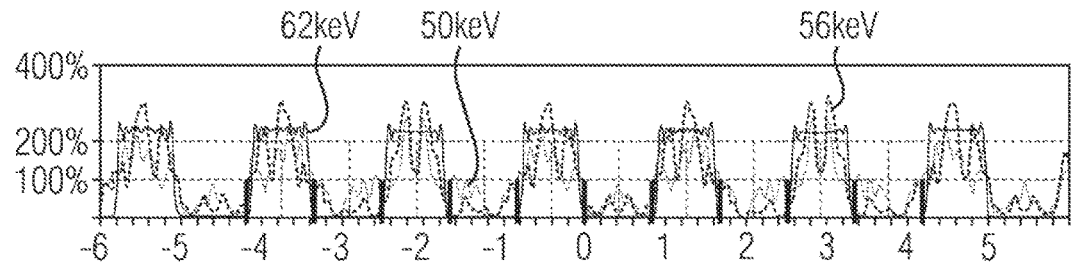
FIG. 20 shows in a graph according to FIG. 18 the interference pattern of the phase grating according to FIG. 17.

FIG. 20 shows—again analogously to the graphs in FIG. 18—the interference pattern which was obtained from the simulation "%14bx3_1.29x1.33_L4" for the layout according to FIG. 17. This layout and the layout (FIG. 16) underlying the simulation "%14bx2_0.57x2.5_L4" have inverted phase deviations and act in the case of longer distances. The figure shows that with these layouts only every second or third interference maximum is like the other.

The layouts shown in the FIGS. 16 and 17 can be produced comparatively easily. Aspect ratios of 55 or 59 can be attained.

The invention is not limited to the exemplary embodiments described above. Instead, a person skilled in the art can derive other variants of the invention herefrom without departing from the subject matter of the invention. In particular, all individual features described in conjunction with the exemplary embodiments can, moreover, be combined with each other in some other way without departing from the subject matter of the invention.

Annex 1: Properties of the Layouts of the Phase Grating $G_1$ According to FIGS. 7 to 17

TABLE 1.1 grating constant $p_1$ and geometry of the layout strips (sequence of phase deviations at the design energy, based on $2\pi$; strip width, based on the grating constant $p_1$)

| Designation | $p_1$/μm | Strip geometry: phase deviation [ . . . $2\pi$] | width [ . . . p1] |
|---|---|---|---|
| %4c_0.50 | 2.582 | (0, 1)/4 | (1, 1)/2 |
| %4bx2_0.50 | 5.164 | (0, 1, 1, 0)/2 | (1, 1, 1, 1)/4 |
| %4bx2_0.50x3 | 2.981 | (0, 1, 1, 0)/2 | (1, 1, 1, 1)/4 |
| %4bx2_0.50x5 | 2.309 | (0, 1, 1, 0)/2 | (1, 1, 1, 1)/4 |
| %4bx2_0.50x7 | 1.952 | (0, 1, 1, 0)/2 | (1, 1, 1, 1)/4 |
| %4bx2_0.50x9 | 1.721 | (0, 1, 1, 0)/2 | (1, 1, 1, 1)/4 |
| %8c_0.25_L3 | 3.651 | (0, 1, 4, 1)/8 | (1, 1, 1, 1)/4 |
| %8cx2_1.00_L2 | 3.651 | (0, 1, 1, 1)/2 | (1, 1, 1, 1)/4 |
| %8cx2_1.00x3_L3_inv-100 | 2.108 | (1, 0, 2, 0)/2 | (2, 1, 4, 1)/8 |
| %8cx2_1.00x3_L3_inv-200 | 2.108 | (1, 0, 4, 1)/2 | (2, 1, 4, 1)/8 |
| %8cx2_1.00x3_L3_adj-100 | 2.108 | (0, 1, 3, 1)/2 | (2, 1, 4, 1)/8 |
| %14b_0.14_L4_inv | 4.830 | (4, 5, 0, 3, 0.5, 4)/7 | (1, 1, . . . , 1)/7 |
| %14bx2_0.57_L4_inv | 4.830 | (4, 5, 0, 3, 0.5, 4)/7 | (1, 1, . . . , 1)/7 |
| %14bx3_1.29_L4_inv | 4.830 | (4, 5, 0, 3, 0.5, 4)/7 | (1, 1, . . . , 1)/7 |
| %14bx2_0.57x2.5_L4 | 3.055 | (6, 5, 3, 0, 3, 5, 6)/7 | (1, 1, . . . , 1)/7 |
| %14bx3_1.29x1.33_L4 | 4.183 | (6, 5, 3, 0, 3, 5, 6)/7 | (1, 1, . . . , 1)/7 |

TABLE 1.2

Maximum material height $h_{max}$, basic material, angle of exposure $\alpha$, grating height $H_1$ and aspect ratio R

| Designation | $h_{max}$ [μm] | Basic material | $\alpha$ | $H_1$ [μm] | R |
|---|---|---|---|---|---|
| %4c_0.50 | 10.9 | Ni | 20° | 16.4 | 21 |
| %4bx2_0.50 | 21.8 | Ni | 20° | 27.3 | 35 |
| %4bx2_0.50x3 | 21.8 | Ni | 20° | 27.3 | 35 |
| %4bx2_0.50x5 | 21.8 | Ni | 20° | 27.3 | 35 |
| %4bx2_0.50x7 | 21.8 | Ni | 20° | 27.3 | 35 |
| %4bx2_0.50x9 | 21.8 | Ni | 20° | 27.3 | 35 |
| %8c_0.25_L3 | 21.8 | Ni | 20° | 27.3 | 35 |
| %8cx2_1.00_L2 | 21.8 | Ni | 20° | 27.3 | 35 |
| %8cx2_1.00x3_L3_inv-100 | 24.7 | Au | 20° | 40.5 | 85 |
| %8cx2_1.00x3_L3_inv-200 | 49.4 | Au | 20° | 66.6 | 133 |
| %8cx2_1.00x3_L3_adj-100 | 65.3 | Ni | 12° | 74.1 | 95 |
| %14b_0.14_L4_inv | 31.1 | Ni | 20° | 35.6 | 55 |
| %14bx2_0.57_L4_inv | 31.1 | Ni | 20° | 35.6 | 55 |
| %14bx3_1.29_L4_inv | 31.1 | Ni | 20° | 35.6 | 55 |
| %14bx2_0.57x2.5_L4 | 37.3 | Ni | 12° | 45.8 | 59 |
| %14bx3_1.29x1.33_L4 | 37.3 | Ni | 12° | 45.8 | 59 |

Annex 2: Boundary Conditions for the Simulations

TABLE 2.1 grating constants $p_0$ and $p_2$ and performance factor.

| Designation | $p_0$ [μm] | $p_2$ [μm] | f |
|---|---|---|---|
| %4c__0.50 | 15.5 | 3.098 | 0.50 |
| %4bx2__0.50 | 15.5 | 3.098 | 0.50 |
| %4bx2__0.50x3 | 8.9 | 1.789 | 1.50 |
| %4bx2__0.50x5 | 6.9 | 1.386 | 2.50 |
| %4bx2__0.50x7 | 5.9 | 1.171 | 3.50 |
| %4bx2__0.50x9 | 5.2 | 1.033 | 4.50 |
| %8c__0.25__L3 | 21.9 | 4.382 | 0.25 |
| %8cx2__1.00__L2 | 11.0 | 2.191 | 1.00 |
| %8cx2__1.00x3__L3__inv-100 | 6.3 | 1.265 | 3.00 |
| %8cx2__1.00x3__L3__inv-200 | 6.3 | 1.265 | 3.00 |
| %8cx2__1.00x3__L3__adj-100 | 6.3 | 1.265 | 3.00 |
| %14b__0.14__L4__inv | 29.0 | 5.796 | 0.14 |
| %14bx2__0.57__L4__inv | 14.5 | 2.898 | 0.57 |
| %14bx3__1.29__L4__inv | 9.7 | 1.932 | 1.29 |
| %14bx2__0.57x2.5__L4 | 9.2 | 1.833 | 1.43 |
| %14bx3__1.29x1.33__L4 | 8.4 | 1.673 | 1.71 |

Annex 3: Performance Data of the Layouts According to FIG. 7 to 17 from Simulation

TABLE 3.1 visibility S for "VOF" (punctiform radiation source, filtered X-ray spectrum), "V50F" (coherence grating $G_0$ with 50% duty cycle, filtered X-ray spectrum) and "V50U" (coherence grating $G_0$ with 50% duty cycle, unfiltered X-ray spectrum)

| | Visibility V | | |
|---|---|---|---|
| Designation | $V = V_A$ VOF | $V = V_B$ V50F | $V = V_C$ V50U |
| %4c__0.50 | 79.4% | 48.2% | 40.8% |
| %4bx2__0.50 | 77.3% | 47.2% | 38.0% |
| %4bx2__0.50x3 | 63.2% | 41.8% | 29.4% |
| %4bx2__0.50x5 | 56.8% | 37.3% | 27.6% |
| %4bx2__0.50x7 | 50.5% | 33.4% | 28.1% |
| %4bx2__0.50x9 | 44.2% | 29.7% | 27.0% |
| %8c__0.25__L3 | 86.5% | 65.9% | 46.1% |
| %8cx2__1.00__L2 | 77.8% | 49.6% | 42.6% |
| %8cx2__1.00x3__L3__inv-100 | 63.2% | 40.8% | 28.5% |
| %8cx2__1.00x3__L3__inv-200 | 70.4% | 46.3% | 33.6% |
| %8cx2__1.00x3__L3__adj-100 | 70.3% | 44.6% | 34.5% |
| %14b__0.14__L4__inv | 86.3% | 72.9% | 56.4% |
| %14bx2__0.57__L4__inv | 85.0% | 62.5% | 53.1% |
| %14bx3__1.29__L4__inv | 73.9% | 48.6% | 39.3% |
| %14bx2__0.57x2.5__L4 | 66.7% | 46.8% | 28.7% |
| %14bx3__1.29x1.33__L4 | 70.6% | 46.4% | 29.4% |

TABLE 3.2

Transmission T for "F" (filtered X-ray spectrum) or "U" (unfiltered X-ray spectrum).

| | Transmission T | |
|---|---|---|
| Designation | $T = T_F$ F | $T = T_U$ U |
| %4c__0.50 | 99.0% | 98.4% |
| %4bx2__0.50 | 98.4% | 97.7% |
| %4bx2__0.50x3 | 98.2% | 97.6% |
| %4bx2__0.50x5 | 97.8% | 97.2% |
| %4bx2__0.50x7 | 97.6% | 96.1% |
| %4bx2__0.50x9 | 97.4% | 96.9% |
| %8c__0.25__L3 | 98.5% | 97.7% |
| %8cx2__1.00__L2 | 97.6% | 96.5% |

TABLE 3.2-continued

Transmission T for "F" (filtered X-ray spectrum) or "U" (unfiltered X-ray spectrum).

| | Transmission T | |
|---|---|---|
| Designation | $T = T_F$ F | $T = T_U$ U |
| %8cx2__1.00x3__L3__inv-100 | 86.9% | 81.6% |
| %8cx2__1.00x3__L3__inv-200 | 79.7% | 73.0% |
| %8cx2__1.00x3__L3__adj-100 | 93.6% | 90.7% |
| %14b__0.14__L4__inv | 97.3% | 95.9% |
| %14bx2__0.57__L4__inv | 97.0% | 95.8% |
| %14bx3__1.29__L4__inv | 97.1% | 95.9% |
| %14bx2__0.57x2.5__L4 | 95.1% | 93.0% |
| %14bx3__1.29x1.33__L4 | 96.1% | 94.2% |

TABLE 3.3

Efficiency for "VOF" (punctiform radiation source, filtered X-ray spectrum; $V = V_A$; $T = T_F$), "V50F" (coherence grating $G_0$ with 50% duty cycle, filtered X-ray spectrum; $V = V_B$; $T = T_F$) and "V50U" (coherence grating $G_0$ with 50% duty cycle, unfiltered X-ray spectrum; $V = V_C$; $T = T_U$); valid relationship $S \propto f^{1/2}$ was used for constant distance $d_{12}$, moreover

| | Efficiency $(S \cdot V)^2 T$ | | |
|---|---|---|---|
| Designation | $f \cdot V_A^2 T_F$ VOF | $f \cdot V_B^2 T_F$ V50F | $f \cdot V_C^2 T_U$ V50U |
| %4c__0.50 | 31.2% | 11.5% | 8.2% |
| %4bx2__0.50 | 29.4% | 11.0% | 7.1% |
| %4bx2__0.50x3 | 58.9% | 25.8% | 12.7% |
| %4bx2__0.50x5 | 78.8% | 34.0% | 18.6% |
| %4bx2__0.50x7 | 87.2% | 38.1% | 26.5% |
| %4bx2__0.50x9 | 85.6% | 38.7% | 31.8% |
| %8c__0.25__L3 | 18.4% | 10.7% | 5.2% |
| %8cx2__1.00__L2 | 59.1% | 24.0% | 17.5% |
| %8cx2__1.00x3__L3__inv-100 | 104.3% | 43.3% | 19.8% |
| %8cx2__1.00x3__L3__inv-200 | 118.3% | 51.3% | 24.7% |
| %8cx2__1.00x3__L3__adj-100 | 138.6% | 55.9% | 32.4% |
| %14b__0.14__L4__inv | 10.4% | 7.4% | 4.4% |
| %14bx2__0.57__L4__inv | 40.1% | 21.6% | 15.4% |
| %14bx3__1.29__L4__inv | 68.2% | 29.5% | 19.1% |
| %14bx2__0.57x2.5__L4 | 60.4% | 29.7% | 10.9% |
| %14bx3__1.29x1.33__L4 | 82.2% | 35.4% | 13.9% |

Annex 4: Physical Foundations

The phase contrast of an X-ray image visualizes different phase speeds $c_p = c_0/(1-\delta) \approx c_0(1+\delta)$ owing to the material-dependent refractive index $n = 1 - \delta + i\beta$.

The transmission T behind the patient is determined by the intensity ratio $T = I/I_0$, where $I_0$ is the average intensity without $G_1$ and $G_2$. The noise (represented by the standard deviation $\sigma_\varphi$) is proportional to $(\Delta t\, I_0)^{-2}$. Four times the dose $\Delta t\, I_0$ is required therefore to halve the noise. With differential phase contrast (and also dark field images) a proportional dependency of the noise $\sigma_\varphi$ on the strip phase $\varphi$ (where V is the (strip) visibility or visibility results, where $$V = (I_{max} - I_{min})/(I_{max} - I_{min})$$

The variables $I_{max}$ and $I_{min}$ designate the maximum/minimum intensities as a function of the x-position of a shiftable $G_0$:

$$\sigma_\varphi^2 \propto 1/(\Delta t\, I_0\, V^2\, T),$$

where visibility V and transmission T can each vary within the limits 0-100%.

To keep the noise at a specific value, $\Delta t\, I_0\, V^2\, T$ must remain unchanged therefore. An efficiency level $\eta_\varphi$ of the lens system behind the patient can be defined as:

$$\eta_\varphi = V^2\, T \text{ where } \eta_\varphi \in [0;1]$$

One aim of the present application is to optimize $\eta_\varphi$, i.e., to achieve a dose minimization with given $\sigma_\varphi$ (in contrast to $\sigma_\Phi$, or $\sigma_{\Phi'}$), where $\Phi$ designates the phase of the actual wave front and $\Phi'$ its spatial change $\Phi' = \partial\Phi/\partial x$. $\Phi'$ is given by $$\Phi' = \partial\Phi/\partial x = \varphi p_{2L}/(\lambda d_{1L})$$

With the definition of the sensitivity S as $S = d_{12}/p_2$ the following applies at given design wavelength $\lambda = \lambda_D$ $$\sigma_{\Phi'} \propto \sigma_\varphi / S$$

The higher the sensitivity, the lower the noise is therefore. From $$\sigma_{\Phi'}^2 \propto \sigma_\varphi^2/S^2 \propto 1/(\Delta t\, I_0 S^2 V^2 T)$$

it follows, as above in the case of predefined noise $\sigma_{\Phi'}$, that the dose $\Delta t \cdot I_0$ is proportional to the efficiency $$\eta = \eta_{\Phi'} = S^2 V^2 T$$

The sensitivity factor f of the phase grating $G_1$ results from $d_{12} = f \cdot p_2^2/\pi_D$ and is linked to the sensitivity S by $S = f \cdot p_2/\lambda_D$.

The invention claimed is:

1. A phase grating for a phase contrast X-ray imaging, the phase grating comprising:
   a transverse surface to be aligned substantially transversely with respect to a radiation incidence direction, said transverse surface being spanned by an x-axis and a y-axis perpendicular to said x-axis;
   a multiplicity of grating webs composed of a basic material and alternately arranged with optically denser interspaces, said grating webs dividing said transverse surface into grating strips that are in each case elongated in a y-direction of said y-axis and that are lined up parallel alongside one another in an x-direction of said x-axis;
   at least one of said grating webs extending within said transverse surface across a plurality of said grating strips; and
   the phase grating, at each said grating strip along a z-axis that extends perpendicularly to said transverse surface, having a homogeneous total thickness of said basic material that differs between mutually adjacent said grating strips.

2. The phase grating according to claim 1, wherein said grating webs are each formed as oblique prisms inclined in the y-direction, said oblique prisms having a base surface and a top surface located in end faces of the phase grating parallel to said transverse surface.

3. The phase grating according to claim 2, wherein said grating webs are designed and arranged such that a material structure that repeats itself in the y-direction with a y period length results in each grating strip, and wherein said grating webs are inclined in the y-direction such that the top surface of each grating opposing the base surface is offset with respect to the base surface by a whole number of period.

4. The phase grating according to claim 3, wherein the top surface of each grating web opposing the base surface is offset with respect to the base surface by exactly one period length.

5. The phase grating according to claim 1, wherein each said grating web adjoins the interspaces arranged between said grating webs by way of two side surfaces respectively, and wherein said side surfaces alternate from first partial surfaces, which are oriented parallel to the y-axis, and second partial surfaces, which are oriented parallel or diagonal to the x-axis.

6. The phase grating according to claim 5, wherein every other said partial surface extends over a whole number of grating strips in the x-direction.

7. The phase grating according to claim 1, wherein each said grating web within the transverse surface runs in alternating sections with a diagonal preferred direction in a positive y-direction and in a negative y-direction respectively.

8. The phase grating according to claim 1, wherein the total thickness of the basic material, measured along the z-axis, varies between at least three discrete values.

9. A phase contrast X-ray imaging device, comprising:
   an X-ray radiation source;
   an X-ray detector having a one-dimensional or two-dimensional arrangement of pixels; and
   a phase grating according to claim 1 disposed between said X-ray radiation source and said X-ray detector.

10. The X-ray imaging device according to claim 9, comprising a coherence grating interposed between said X-ray radiation source and said phase grating.

11. The X-ray imaging device according to claim 9, comprising an analysis grating interposed between said phase grating and said X-ray detector.

* * * * *